(12) United States Patent
Fischer et al.

(10) Patent No.: US 11,261,262 B2
(45) Date of Patent: Mar. 1, 2022

(54) READILY ISOLATED BISPECIFIC BINDING MOLECULES WITH NATIVE FORMAT HAVING MUTATED CONSTANT REGIONS

(71) Applicant: Novimmune S.A., Geneva (CH)

(72) Inventors: Nicolas Fischer, Geneva (CH); Giovanni Magistrelli, Cessy (FR); Francois Rousseau, Collonges sous Saleve (FR); Krzysztof Masternak, Mollens (CH); Pauline Malinge, Cernex (FR)

(73) Assignee: NovImmune SA, Geneva (CH)

( * ) Notice: Subject to any disclaimer, the term of this patent is extended or adjusted under 35 U.S.C. 154(b) by 0 days.

(21) Appl. No.: 14/475,892

(22) Filed: Sep. 3, 2014

(65) Prior Publication Data

US 2015/0094451 A1  Apr. 2, 2015

Related U.S. Application Data

(60) Provisional application No. 61/872,932, filed on Sep. 3, 2013.

(51) Int. Cl.
  *C07K 16/46*  (2006.01)
  *C07K 16/28*  (2006.01)
  *C07K 16/24*  (2006.01)

(52) U.S. Cl.
  CPC .......... *C07K 16/468* (2013.01); *C07K 16/244* (2013.01); *C07K 16/2809* (2013.01); *C07K 2317/21* (2013.01); *C07K 2317/31* (2013.01); *C07K 2317/50* (2013.01); *C07K 2317/522* (2013.01); *C07K 2317/526* (2013.01); *C07K 2317/622* (2013.01); *C07K 2317/94* (2013.01)

(58) Field of Classification Search
  CPC .............. C07K 16/468; C07K 16/2809; C07K 2317/21; C07K 2317/31; C07K 2317/52; C07K 2317/522; C07K 2317/526; C07K 2317/622; C07K 2317/94; C07K 16/244; C07K 1/22; C07K 2317/50; C12N 15/67; C12P 21/02
  See application file for complete search history.

(56) References Cited

U.S. PATENT DOCUMENTS

| | | | |
|---|---|---|---|
| 5,945,311 A | 8/1999 | Lindhofer et al. | |
| 8,216,805 B2 | 7/2012 | Carter et al. | |
| 9,815,909 B2* | 11/2017 | Fischer | C07K 16/468 |
| 2010/0331527 A1* | 12/2010 | Davis | C07K 16/2809 |
| | | | 530/387.3 |
| 2015/0239991 A1* | 8/2015 | Blein | B01D 15/3809 |
| | | | 530/389.5 |

FOREIGN PATENT DOCUMENTS

EP        2522724 A1   11/2012
WO   WO 2014/145806 A2   9/2014

OTHER PUBLICATIONS

Marvin et al., Acta Pharmacologica Sinica 26(6): 649-658, Jun. 2005.*
"www.captureselect.com/shopfiles/upload/files/Product_Sheet_CaptureSelect_IgG-CH1.pdf" Mar. 9, 2011, pp. 1-4; retrieved on Jun. 16, 2011.
Moretti, et al. "BEAT® the bispecific challenge: a novel and efficient platform for the expression of bispecific IgGs," BMC Proceedings, 7(Suppl 6): 09 (2013).
Garber, E. and S.J. Demarest (Apr. 13, 2007) "A broad range of Fab stabilities within a host of therapeutic IgGs" *Biochem Biophys Res Commun*, 355(3):751-757.
IMGT "Correspondence between the IMGT unique numbering for C-DOMAIN, the IMGT exon numbering, the Eu and Kabat numberings: Human IGHG" (updated Aug. 13, 2014) [online]. Retrieved from the Internet: http://www.imgt.org/IMGTScientificChart/Numbering/Hu_IGHGNber.html; retrieved on Mar. 17, 2015, 4 pages.
Lindhofer, H. et al. (1995) "Preferential Species-Restricted Heavy/Light Chain Pairing in Rat/Mouse Quadromas. Implications for a Single-Step Purification of Bispecific Antibodies" *J Immunol*, 155:219-225.
LeFranc, M-P, "Immunoglobulin and T cell receptor genes: IMGT and the birth and rise of immunoinformatics," Front Immunol., 5: 22 (2014), 22 pages; doi: 10.3389/fimmu.2014.00022.
MAN0017191_ CaptureSelect™ Antibody Affinity Resins Product Information Sheet, Sep. 25, 2018, 4 pages.

* cited by examiner

*Primary Examiner* — Phuong Huynh
(74) *Attorney, Agent, or Firm* — Cooley LLP; Cynthia A. Kozakiewicz; Ivor R. Elrifi

(57) ABSTRACT

The invention provides heterodimer bispecific antigen-binding molecules that include a first polypeptide that does not include an IgG CH1 domain and a second polypeptide where there is at least one mutation in the IgG CH3 domain that abolishes the ability of the second polypeptide to bind CH3-specific affinity media such that the first and second polypeptides have different affinities with respect to CH1 and CH3 specific affinity reagents that allows rapid isolation by differential binding. The invention also provides bispecific antibodies that have CH1 and CH3 regions with different affinities with respect to affinity reagents that allows rapid isolation by differential binding. The invention also concerns bispecific antibodies which are heterodimers of two IgG heavy chains that differ by at least two amino acids that allow for rapid isolation based on a differential affinity of one mutated heavy chain and a second mutated heavy chain toward two different affinity reagents.

23 Claims, 24 Drawing Sheets
Specification includes a Sequence Listing.

Figure 2

| IgG1 CH1 mutants | ... | P | V | T | S (40) | W | N | S | G | A | L | T (47) | S |
|---|---|---|---|---|---|---|---|---|---|---|---|---|---|
| M2 | | | | | T | | | | | | | | S |
| 76 | | | | | Q | | | | | | | | |
| 77 | | | | | K | | | | | | | | |
| 78 | | | | | A | | | | | | | | |
| 79 | | | | | | | | | | | | | E |
| 80 | | | | | Q | | | | | | | | Q |
| 90 | | | | | E | | | | | | | | |
| 91 | | | | | | | | | | | | | Q |
| 92 | | | | | A | | | | | | | | A |
| 93 | | | | | | | | | | | | | A |
| 94 | | | | | | | | | | | | | K |

Figure 3

| IgG1 CH3 mutants | ... | A | V | E | W | E (265) | S (266) | N | G | Q | P (270) | E | N |
|---|---|---|---|---|---|---|---|---|---|---|---|---|---|
| B11 | | | | | | Q | | | | | T | | |
| 74 | | | | | | | | | | | T | | |
| 75 | | | | | | Q | R | | | | | | |
| 81 | | | | | | A | R | | | | | | |
| 82 | | | | | | A | A | | | | A | | |
| 83 | | | | | | | | | | | | | |
| 84 | | | | | | Q | R | | | | A | | |
| 85 | | | | | | A | A | | | | | | |
| 86 | | | | | | A | A | | | | A | | |
| 87 | | | | | | A | A | | | | | | |
| 88 | | | | | | | R | | | | T | | |
| 89 | | | | | | | | | | | | | |

A

B

READILY ISOLATED BISPECIFIC BINDING MOLECULES WITH NATIVE FORMAT HAVING MUTATED CONSTANT REGIONS

RELATED APPLICATIONS

This application claims the benefit of U.S. Provisional Application No. 61/872,932, filed Sep. 3, 2013. The contents of this application are hereby incorporated by reference in their entirety.

INCORPORATION OF SEQUENCE LISTING

The contents of the text file named "NOVI033001US ST25.txt", which was created on Dec. 16, 2014 and is 18.8 KB in size, are hereby incorporated by reference in their entirety.

FIELD OF THE INVENTION

The invention provides heterodimer bispecific antigen-binding molecules that include a first polypeptide that does not include an IgG CH1 domain and a second polypeptide having an immunoglobulin constant region where there is at least one mutation in the IgG CH3 domain that abolishes the ability of the second polypeptide to bind CH3-specific affinity media such that the first and second polypeptides have different affinities with respect to CH1 and CH3 specific affinity reagents that allows rapid isolation by differential binding of the first and second polypeptides to these affinity reagents. The invention also provides bispecific antibodies that have IgG CH1 and CH3 regions with different affinities with respect to affinity reagents that allows rapid isolation by differential binding of the IgG regions to these affinity reagents. The invention also concerns bispecific antibodies which are heterodimers of heavy chains, i.e., two immunoglobulin heavy chains that differ by at least two amino acids that allow for the isolation of the bispecific antibody based on a differential affinity of one mutated immunoglobulin heavy chain and a second mutated immunoglobulin heavy chain toward two different affinity reagents.

BACKGROUND OF THE INVENTION

Antibodies are multifunctional molecules carrying a unique binding specificity for a target antigen or multiple targets and having the capacity to interact with the immune system via mechanisms that are antigen-independent. Many currently used biological therapeutics for cancer are monoclonal antibodies directed against antigens that are typically overexpressed on the targeted cancer cell. When such antibodies bind tumor cells, they may trigger antibody-dependent cellular cytotoxicity (ADCC) or complement-dependent cytotoxicity (CDC). Unfortunately, cancerous cells often develop mechanisms to suppress these normal immune responses. In addition, targeting or neutralizing a single protein is not always sufficient to achieve efficacy in certain diseases which limits the therapeutic use of monoclonal antibodies. It is increasingly clear that in a number of indications neutralizing one component of a biological system is not sufficient to achieve efficacy.

Accordingly, there remains a need for a bispecific antibody format, in particular for therapeutic applications, that minimizes some or all of the disadvantages mentioned above.

SUMMARY OF THE INVENTION

The invention is based at least in part on heterodimeric antigen-binding polypeptides where the first polypeptide does not include an immunoglobulin (Ig) CH1 constant region and a second polypeptide that has an IgG constant region where the CH3 region differs by at least 1 amino acid. The lack of a CH1 region and the one CED amino acid difference results in an improved ability to quickly and effectively isolate the protein using a two-step purification, because the difference results first in a differential ability of the IgG CH1 domain sequences to bind a ligand that specifically interact with the IgG CH1 domain and which is used as a component of an affinity resin like the CaptureSelect® IgG-CH1 affinity reagent (aldehyde-activated agarose resin that specifically binds to human IgG-CH1 region) and then a differential ability of the IgG CED domain sequences to bind a ligand that specifically interact with the IgG CH3 domain and which is used as a component of an affinity resin like the CaptureSelect® IgG Fc XL affinity reagent (aldehyde-activated agarose resin that specifically binds to human IgG-CH3 region).

In some embodiments, the first and second polypeptides are both immunoglobulin sequences or are derived from immunoglobulin sequences. In the embodiments where the heterodimeric antigen-binding polypeptide is a bispecific antibody or antigen-binding fragment thereof, the invention is based at least in part on employing two immunoglobulin heavy chain constant domain sequences that differ by at least 2 amino acids in a bispecific antigen-binding protein. The two amino acid difference results in an improved ability to quickly and effectively isolate the protein using a two-step purification, because the difference results first in a differential ability of the IgG CH1 domain sequences to bind a ligand that specifically interact with the IgG CH1 domain and which is used as a component of an affinity resin like the CaptureSelect® IgG-CH1 affinity reagent and then a differential ability of the IgG CH3 domain sequences to bind a ligand that specifically interact with the IgG CH3 domain and which is used as a component of an affinity resin like the CaptureSelect® IgG Fc XL affinity reagent.

In some embodiments, the heterodimeric bispecific antigen-binding protein includes a first polypeptide comprising, from N-terminal to C-terminal a first epitope-binding region that selectively binds a first epitope and an immunoglobulin constant region that does not include the constant CH1 region of a human IgG selected from IgG1, IgG2, IgG3 and IgG4; and a second polypeptide comprising, from N-terminal to C-terminal, a second epitope-binding region that selectively binds a second epitope and an immunoglobulin constant region that comprises at least a CH3 region of a human IgG selected from IgG1, IgG2, IgG3 and IgG4, wherein the CH3 region of the second polypeptide comprises a modification that reduces or eliminates interaction of the CH3 domain to the ligand of an affinity reagent binding to the human IgG1, IgG2, IgG3 and IgG4 CH3 domain.

In some embodiments, the first and second polypeptides are derived from human IgG heavy chains. In some embodiments, the heterodimeric bispecific protein also includes an immunoglobulin light chain. In some embodiments, the immunoglobulin light chain comprises a human immunoglobulin light chain or is derived from a human immunoglobulin light chain. In some embodiments, the first and second polypeptides comprise polypeptide sequences that are derived from human IgG1 heavy chains.

In some embodiments, the first polypeptide comprises a fusion protein. In some embodiments, the fusion protein comprises an Fc immunoglobulin polypeptide sequence or a polypeptide sequence that is derived from an Fc immunoglobulin polypeptide. In some embodiments, the first polypeptide comprises a single chain variable (scFv) antibody fragment. In some embodiments, the first polypeptide is selected from the group consisting of cytokine-Fc fusion polypeptide such as, by way of nonlimiting example, human IL-6-Fc, human IL-2-Fc, human TN F-Fc, human IL-10-Fc, human IL-4-Fc, human GCSF-Fc, human GM-CSF-Fc, human IFNα-Fc, human IFNβ-Fc, or human IFNγ-Fc.

In some embodiments, the CH3 domain of the second polypeptide is an IgG CH3 domain, and wherein the modification in the IgG1 CH3 domain of the second polypeptide comprises an E265A mutation in the IMGT exon numbering system or a E265Q mutation in the IMGT exon numbering system, a P270T in the IMGT exon numbering system or a combination thereof.

In some embodiments, the CH3 domain of the second polypeptide is an IgG2 CH3 domain, and wherein the modification in the IgG2 CH3 domain of the second polypeptide comprises an E261A mutation in the IMGT exon numbering system or a E261Q mutation in the IMGT exon numbering system, a P266T in the IMGT exon numbering system or a combination thereof.

In some embodiments, the CH3 domain of the second polypeptide is an IgG3 CH3 domain, and wherein the modification in the IgG3 CH3 domain of the second polypeptide comprises an E312A mutation in the IMGT exon numbering system or a E312Q mutation in the IMGT exon numbering system, a P317T in the IMGT exon numbering system or a combination thereof.

In some embodiments, the CH3 domain of the second polypeptide is an IgG4 CH3 domain, and wherein the modification in the IgG4 CH3 domain of the second polypeptide comprises an E262A mutation in the IMGT exon numbering system or a E262Q mutation in the IMGT exon numbering system, a P267T in the IMGT exon numbering system or a combination thereof.

In some embodiments, the affinity reagent binding to the human IgG1, IgG2, IgG3 and IgG4 CH1 domain comprises an affinity resin. In some embodiments, the affinity resin is a CaptureSelect® IgG-CH1 resin.

In some embodiments, the affinity reagent binding to the human IgG1, IgG2, IgG3 and IgG4 CH3 domain comprises an affinity resin. In some embodiments, the affinity resin is a CaptureSelect® FcXL resin.

In one embodiment, the IgG1 CH3 region from the second polypeptide comprises an E265A modification. As used herein, an "E265A" mutation is one in which the WT residue, glutamic acid, at position 265 is replaced with alanine (i.e., E→A mutation at residue 265).

In one embodiment, the IgG CH3 region from the second polypeptide comprises an E265Q and P270T modification by IMGT exon numbering. As used herein, an "E265Q" mutation is one in which the WT residue, glutamic acid, at position 265 is replaced with glutamine (i.e., E→Q mutation at residue 265), a "P270T" mutation is one in which the WT residue, proline, at position 270 is replaced with threonine (i.e., P→T mutation at residue 270).

In one embodiment, the IgG2 CH3 region from the second polypeptide comprises an E261A modification. As used herein, an "E261A" mutation is one in which the WT residue, glutamic acid, at position 261 is replaced with alanine (i.e., E→A mutation at residue 261).

In one embodiment, the IgG2 CH3 region from the second polypeptide comprises an E261Q and P266T modification by IMGT exon numbering. As used herein, an "E261Q" mutation is one in which the WT residue, glutamic acid, at position 261 is replaced with glutamine (i.e., E→Q mutation at residue 261), a "P266T" mutation is one in which the WT residue, proline, at position 266 is replaced with threonine (i.e., P→T mutation at residue 266).

In one embodiment, the IgG3 CH3 region from the second polypeptide comprises an E312A modification. As used herein, an "E312A" mutation is one in which the WT residue, glutamic acid, at position 312 is replaced with alanine (i.e., E→A mutation at residue 312).

In one embodiment, the IgG3 CH3 region from the second polypeptide comprises an E312Q and P317T modification by IMGT exon numbering. As used herein, an "E312Q" mutation is one in which the WT residue, glutamic acid, at position 312 is replaced with glutamine (i.e., E→Q mutation at residue 312), a "P317T" mutation is one in which the WT residue, proline, at position 317 is replaced with threonine (i.e., P→T mutation at residue 317).

In one embodiment, the IgG4 CH3 region from the second polypeptide comprises an E262A modification. As used herein, an "E262A" mutation is one in which the WT residue, glutamic acid, at position 262 is replaced with alanine (i.e., E→A mutation at residue 262).

In one embodiment, the IgG4 CH3 region from the second polypeptide comprises an E262Q and P267T modification by IMGT exon numbering. As used herein, an "E262Q" mutation is one in which the WT residue, glutamic acid, at position 262 is replaced with glutamine (i.e., E→Q mutation at residue 262), a "P267I" mutation is one in which the WT residue, proline, at position 267 is replaced with threonine (i.e., P→T mutation at residue 267).

In specific embodiments, the CH3 region from the second polypeptide is selected from SEQ ID NO: 13, SEQ ID NO: 14, SEQ ID NO: 15, SEQ ID NO: 16, SEQ ID NO: 17, SEQ ID NO: 18, SEQ ID NO: 19 and SEQ ID NO: 20.

In one embodiment, the CH3 region from the second polypeptide is or is derived from modified human IgG1 (SEQ ID NO: 13 and 14).

In one embodiment, the CH3 region from the second polypeptide is or is derived from modified human IgG2 (SEQ ID NO: 15 and 16).

In one embodiment, the CH3 region from the second polypeptide is or is derived from a modified human IgG3 (SEQ ID NO: 17 and 18).

In one embodiment, the CH3 region from the second polypeptide is or is derived from a modified human IgG4 (SEQ ID NO: 19 and 20).

In one embodiment, the CH3 domain is a chimeric domain that comprises sequences of two or more of human IgG1, human IgG2, human IgG3 and human IgG4.

In one embodiment, the CH3 domain is from human IgG1, human IgG2, human IgG3, or human IgG4, and the antigen-binding protein further comprises a CH1 domain and a CH2 domain, wherein the CH1 domain and the CH2 domain are independently selected from the group consisting of a human IgG1 CH1 or CH2 domain, a human IgG2 CH1 or CH2 domain, a human IgG3 CH11 or CH2 domain, a human IgG4 CH1 or CH2 domain.

In some embodiments, an antigen-binding protein is provided, comprising a first and a second polypeptide, the first polypeptide comprising, from N-terminal to C-terminal, a first antigen-binding region that selectively binds a first antigen, followed by a constant region that comprises a CH1 region of a human IgG selected from IgG1, IgG2, IgG3, IgG4, and a combination thereof, wherein the CH1 region comprises a modification that reduces or eliminates binding of the CH1 domain to a ligand that specifically interact with the IgG CH1 domain and which is used as a component of an affinity resin like the CaptureSelect® IgG-CH1 affinity reagent, the second polypeptide comprising, from N-terminal to C-terminal, a second antigen-binding region that selectively binds a second antigen, followed by a constant region that comprises a CH3 region of a human IgG selected from IgG1, IgG2, IgG3, IgG4, and a combination thereof, wherein the CH3 region comprises a modification that reduces or eliminates binding of the CH3 domain to a ligand that specifically interact with the IgG CH3 domain and which is used as a component of an affinity resin like the CaptureSelect® IgG Fc XL affinity reagent.

In some embodiments, the heterodimeric bispecific antigen-binding protein includes a first polypeptide comprising, from N-terminal to C-terminal a first epitope-binding region that selectively binds a first epitope and an immunoglobulin constant region that comprises at least a first CH1 region of a human IgG selected from IgG1, IgG2, IgG3 and IgG4, wherein the CH1 region of the first polypeptide comprises a modification that reduces or eliminates binding of the CH1 domain to the ligand of an affinity reagent interacting with the human IgG1. IgG2. IgG3 and IgG4 CH1 domain; and b) a second polypeptide comprising, from N-terminal to C-terminal, a second epitope-binding region that selectively binds a second epitope and an immunoglobulin constant region that comprises at least a CH3 region of a human IgG selected from IgG1, IgG2, IgG3 and IgG4, wherein the CH3 region of the second polypeptide comprises a modification that reduces or eliminates binding of the CH3 domain to the ligand of an affinity reagent interacting with the human IgG1, IgG2, IgG3 and IgG4 CH3 domain.

In some embodiments, the first polypeptide and the second polypeptide are derived from human IgG heavy chains. In some embodiments, the heterodimeric bispecific protein also includes an immunoglobulin light chain. In some embodiments, the immunoglobulin light chain comprises a human immunoglobulin light chain or is derived from a human immunoglobulin light chain. In some embodiments, the first and the second polypeptides are derived from human IgG1 heavy chains.

In some embodiments, the modification in the CH1 domain of the first polypeptide comprises an S40E mutation in the IMGT exon numbering system.

In some embodiments, the CH3 domain of the second polypeptide is an IgG1 CH3 domain, and wherein the modification in the IgG1 CH3 domain of the second polypeptide comprises an E265A mutation in the IMGT exon numbering system or a E265Q mutation in the IMGT exon numbering system, a P270T in the IMGT exon numbering system or a combination thereof.

In some embodiments, the CH3 domain of the second polypeptide is an IgG2 CH3 domain, and wherein the modification in the IgG2 CH3 domain of the second polypeptide comprises an E261A mutation in the IMGT exon numbering system or a E261Q mutation in the IMGT exon numbering system, a P266T in the IMGT exon numbering system or a combination thereof.

In some embodiments, the CH3 domain of the second polypeptide is an IgG3 CH3 domain, and wherein the modification in the IgG3 CH3 domain of the second polypeptide comprises an E312A mutation in the IMGT exon numbering system or a E312Q mutation in the IMGT exon numbering system, a P317T in the IMGT exon numbering system or a combination thereof.

In some embodiments, the CH3 domain of the second polypeptide is an IgG4 CH3 domain, and wherein the modification in the IgG4 CH3 domain of the second polypeptide comprises an E262A mutation in the IMGT exon numbering system or a E262Q mutation in the IMGT exon numbering system, a P267T in the IMGT exon numbering system or a combination thereof.

In some embodiments, the affinity reagent binding to the human IgG1, IgG2, IgG3 and IgG4 CH1 domain comprises an affinity resin. In some embodiments, the affinity resin is a CaptureSelect® IgG-CH1 resin.

In some embodiments, the affinity reagent interacting with the human IgG1, IgG2, IgG3 and IgG4 CH3 domain comprises an affinity resin. In some embodiments, the affinity resin is a CaptureSelect® FcXL resin.

In one embodiment, the CH1 region from the first polypeptide comprises an S40E modification by IMGT exon numbering (IMGT®, the international ImMunoGeneTics Information System®). As used herein, an "S40E" mutation is one in which the wild-type (WT) residue, serine, at position 40 is replaced with a glutamic acid (i.e., S→E mutation at residue 40).

In specific embodiments, the CH1 region from the first polypeptide is selected from, SEQ ID NO: 5, SEQ ID NO: 6, SEQ ID NO: 7 and SEQ ID NO: 8.

In one embodiment, the CH1 region from the first polypeptide is or is derived from a modified human IgG1 (SEQ ID NO: 5).

In one embodiment, the CH1 region from the first polypeptide is or is derived from a modified human IgG2 (SEQ ID NO: 6).

In one embodiment, the CH1 region from the first polypeptide is or is derived from a modified human IgG3 (SEQ ID NO: 7).

In one embodiment, the CH1 region from the first polypeptide is or is derived from a modified human IgG4 (SEQ ID NO: 8).

In one embodiment, the CH1 domain is a chimeric domain that comprises sequences of two or more of human IgG1, human IgG2, human IgG3 and human IgG4.

In one embodiment, the CH1 domain is from human IgG1, human IgG2, human IgG3, or human IgG4, and the antigen-binding protein further comprises a CH2 domain and a CH3 domain, wherein the CH2 domain and the CH3 domain are independently selected from the group consisting of a human IgG1 CH2 or CH3 domain, a human IgG2 CH2 or CH3 domain, a human IgG3 CH2 or CH3 domain, a human IgG4 CH2 or CH3 domain.

In one embodiment, the IgG1 CH3 region from the second polypeptide comprises an E265A modification. As used herein, an "E265A" mutation is one in which the WT residue, glutamic acid, at position 265 is replaced with alanine (i.e., E→A mutation at residue 265).

In one embodiment, the IgG1 CH3 region from the second polypeptide comprises an E265Q and P270T modification by IMGT exon numbering. As used herein, an "E265Q" mutation is one in which the WT residue, glutamic acid, at position 265 is replaced with glutamine (i.e., E→Q mutation at residue 265), a "P270T" mutation is one in which the WT residue, proline, at position 270 is replaced with threonine (i.e., P→T mutation at residue 270).

In one embodiment, the IgG2 CH3 region from the second polypeptide comprises an E261A modification. As used herein, an "E261A" mutation is one in which the WT residue, glutamic acid, at position 261 is replaced with alanine (i.e., E→A mutation at residue 261).

In one embodiment, the IgG2 CH3 region from the second polypeptide comprises an E261Q and P266T modification by IMGT exon numbering. As used herein, an "E261Q" mutation is one in which the WT residue, glutamic acid, at position 261 is replaced with glutamine (i.e., E→Q mutation at residue 261), a "P266T" mutation is one in which the WT residue, proline, at position 266 is replaced with threonine (i.e., P→T mutation at residue 266).

In one embodiment, the IgG3 CH3 region from the second polypeptide comprises an E312A modification. As used herein, an "E312A" mutation is one in which the WT residue, glutamic acid, at position 312 is replaced with alanine (i.e., E→A mutation at residue 312).

In one embodiment, the IgG3 CH3 region from the second polypeptide comprises an E312Q and P317T modification by IMGT exon numbering. As used herein, an "E312Q" mutation is one in which the WT residue, glutamic acid, at position 312 is replaced with glutamine (i.e., E→Q mutation at residue 312), a "P317T" mutation is one in which the WT residue, proline, at position 317 is replaced with threonine (i.e., P→T mutation at residue 317).

In one embodiment, the IgG4 CH3 region from the second polypeptide comprises an E262A modification. As used herein, an "E262A" mutation is one in which the WT residue, glutamic acid, at position 262 is replaced with alanine (i.e., E→A mutation at residue 262).

In one embodiment, the IgG4 CH3 region from the second polypeptide comprises an E262Q and P267T modification by IMGT exon numbering. As used herein, an "E262Q" mutation is one in which the WT residue, glutamic acid, at position 262 is replaced with glutamine (i.e., E→Q mutation at residue 262), a "P267T" mutation is one in which the WT residue, proline, at position 267 is replaced with threonine (i.e., P→T mutation at residue 267).

In specific embodiments, the CH3 region from the second polypeptide is selected from SEQ ID NO: 13, SEQ ID NO: 14, SEQ ID NO: 15, SEQ ID NO: 16, SEQ ID NO: 17, SEQ ID NO: 18, SEQ ID NO: 19 and SEQ ID NO: 20.

In one embodiment, the CH3 region from the second polypeptide is or is derived from modified human IgG1 (SEQ ID NO: 13 and 14).

In one embodiment, the CH3 region from the second polypeptide is or is derived from modified human IgG2 (SEQ ID NO: 15 and 16).

In one embodiment, the CH3 region from the second polypeptide is or is derived from a modified human IgG3 (SEQ ID NO: 17 and 18).

In one embodiment, the CH3 region from the second polypeptide is or is derived from a modified human IgG4 (SEQ ID NO: 19 and 20).

In one embodiment, the CH3 domain is a chimeric domain that comprises sequences of two or more of human IgG1, human IgG2, human IgG3 and human IgG4.

In one embodiment, the CH3 domain is from human IgG1, human IgG2, human IgG3, or human IgG4, and the antigen-binding protein further comprises a CH1 domain and a CH2 domain, wherein the CH11 domain and the CH2 domain are independently selected from the group consisting of a human IgG1 CH1 or CH2 domain, a human IgG2 CH1 or CH2 domain, a human IgG3 CH1 or CH2 domain, a human IgG4 CH1 or CH2 domain.

In one embodiment, the antigen-binding protein further comprises an immunoglobulin light chain.

In other embodiment the immunoglobulin light chain is selected from a human lambda and a human kappa light chain.

In one embodiment, the first and the second antigen-binding regions each comprise at least one complementarity determining region (CDR). In another embodiment, the first and the second antigen-binding regions each comprise at least two CDRs. In another embodiment, the first and the second antigen-binding regions each comprise each comprise three CDRs. In a specific embodiment, the CDRs are from an immunoglobulin heavy chain. In another specific embodiment, the heavy chain is a human heavy chain.

In one embodiment, the first antigen-binding region comprises a first immunoglobulin heavy chain variable domain, and the second antigen-binding region comprises a second immunoglobulin heavy chain variable domain.

In one embodiment, the first and the second immunoglobulin heavy chain variable domains independently comprise a human CDR, a mouse CDR, a rat CDR, a rabbit CDR, a monkey CDR, an ape CDR, a synthetic CDR, and/or a humanized CDR. In one embodiment, the CDR is human and is somatically mutated.

In one embodiment, the first and the second immunoglobulin heavy chain variable domain comprise a human framework region (FR). In one embodiment, the human FR is a somatically mutated human FR.

In one embodiment, the first and/or the second antigen-binding regions are obtained by screening a phage library comprising antibody variable regions for reactivity toward an antigen of interest.

In another embodiment, the first and/or the second antigen-binding regions are obtained by immunizing a non-human animal such as a mouse, a rat, a rabbit, a monkey, or an ape with an antigen of interest and identifying an antibody variable region nucleic acid sequence encoding variable region specific for the antigen of interest.

In another specific embodiment, one or more human immunoglobulin variable region genes are present in the non-human animal extrachromosomally, as a replacement at an endogenous immunoglobulin locus, or as a transgene randomly integrated into the genome of the non-human animal. In one embodiment, the first and/or the second antigen-binding regions are obtained from a hybridoma or a quadroma, in another embodiment from screening immune cells of an immunized non-human animal using cell sorting.

In one embodiment, the antigen-binding protein is a bispecific antibody. In one embodiment, the bispecific antibody is a fully human bispecific antibody and has an affinity for each epitope, independently, in the micromolar, nanomolar, or picomolar range.

In one embodiment, the antigen-binding protein is non-immunogenic or substantially non-immunogenic in a human. In a specific embodiment, the antigen-binding protein lacks a non-native human T-cell epitope. In one embodiment, the modification of the CH1 region is non-immunogenic or substantially non-immunogenic in a human.

In one embodiment, the antigen-binding protein comprises a heavy chain, wherein the heavy chain is non-immunogenic or substantially non-immunogenic in a human.

In one embodiment, the heavy chain has an amino acid sequence that does not contain a non-native T-cell epitope. In one embodiment, the heavy chain comprises an amino acid sequence whose proteolysis cannot form an amino acid sequence of about 9 amino acids that is immunogenic in a human. In a specific embodiment, the human is a human being treated with the antigen-binding protein. In one embodiment, the heavy chain comprises an amino acid sequence whose proteolysis cannot form an amino acid sequence of about 13 to about 17 amino acids that is immunogenic in a human. In a specific embodiment, the human is a human being treated with the antigen-binding protein.

In one aspect, a method for making a bispecific antibody is provided, comprising: obtaining a nucleic acid sequence encoding a first immunoglobulin heavy chain comprising a first variable domain that recognizes a first epitope, wherein the first immunoglobulin heavy chain comprises an IgG1, IgG2, IgG3 or IgG4 isotype constant domain, or a chimeric isotype constant domain thereof, that comprises a modification in its CH1 domain that eradicates or reduces binding to a ligand that specifically interact with the IgG CH1 domain and which is used as a component of an affinity resin like the CaptureSelect® IgG-CH1 affinity reagent; obtaining a nucleic acid sequence encoding a second immunoglobulin heavy chain comprising a second variable domain that recognizes a second epitope, wherein the second immunoglobulin heavy chain comprises an IgG1, IgG2, IgG3 or IgG4 isotype constant domain, or a chimeric isotype constant domain thereof, that comprises a modification in its CH3 domain that eradicates or reduces binding to a ligand that specifically interact with the IgG CH3 domain and which is used as a component of an affinity resin like the CaptureSelect® IgG Fc XL affinity reagent; obtaining a third nucleic acid sequence encoding an immunoglobulin light chain that pairs with the first and the second immunoglobulin heavy chain; introducing the first, second, and third nucleic acid sequences into a mammalian cell; allowing the cell to express an immunoglobulin, and isolating the immunoglobulin using two resins which contain ligands specific of the IgG CH1 domain and IgG CH3 domain like the CaptureSelect® IgG-CH1 affinity reagent and CaptureSelect® IgG Fc XL affinity reagent.

In one embodiment, the cell is selected from a CHO, COS, 293, HeLa, and a retinal cell expressing a viral nucleic acid sequence (e.g., a PERC.6™ cell).

In one aspect, a method for making a bispecific antibody is provided, comprising a step of isolating from a disrupted cell or a mixture of antibodies a bispecific antibody having differentially modified IgG1, IgG2. IgG3 or IgG4 CH1 and CH3 domains, wherein the differentially modified CH1 and CH3 domains are non-immunogenic or substantially non-immunogenic in a human, and wherein the modification results in a bispecific antibody with heterodimeric heavy chains whose monomers have a differential affinity for two different affinity reagents, and the bispecific antibody is isolated from the disrupted cell or the mixture using two steps of purification with two affinity reagents.

Any of the embodiments and aspects described herein can be used in conjunction with one another, unless otherwise indicated or apparent from the context. Other embodiments will become apparent to those skilled in the art from a review of the ensuing description.

BRIEF DESCRIPTION OF THE FIGURES

FIG. 1A is a schematic representation of a two-step asymmetric purification process based on CH1 and CH3 specific chromatography media and the use of a first target-binding polypeptide that does not include a CH1 domain, and a second polypeptide that includes an immunoglobulin constant region and includes a mutation in the CH3 domain that abrogates binding to the CH3 specific media for isolation of bispecific binding molecule composed of the first and second polypeptide. FIG. 1B is a schematic representation of a two-step asymmetric purification process based on CH1 and CH3 specific chromatography media and mutations, which abrogate binding to these media, in the CH1 and CH3 domains of two parental monoclonal antibodies having two different heavy chains and one common light chain for isolation of bispecific antibody composed of two different heavy chains and one common light chain.

FIG. 2 is a table depicting the IgG1 CH1 domain mutations tested in the examples provided below.

FIG. 3 is a table depicting the IgG1 CH3 domain mutations tested in the examples provided below.

DETAILED DESCRIPTION

Figure 1A:
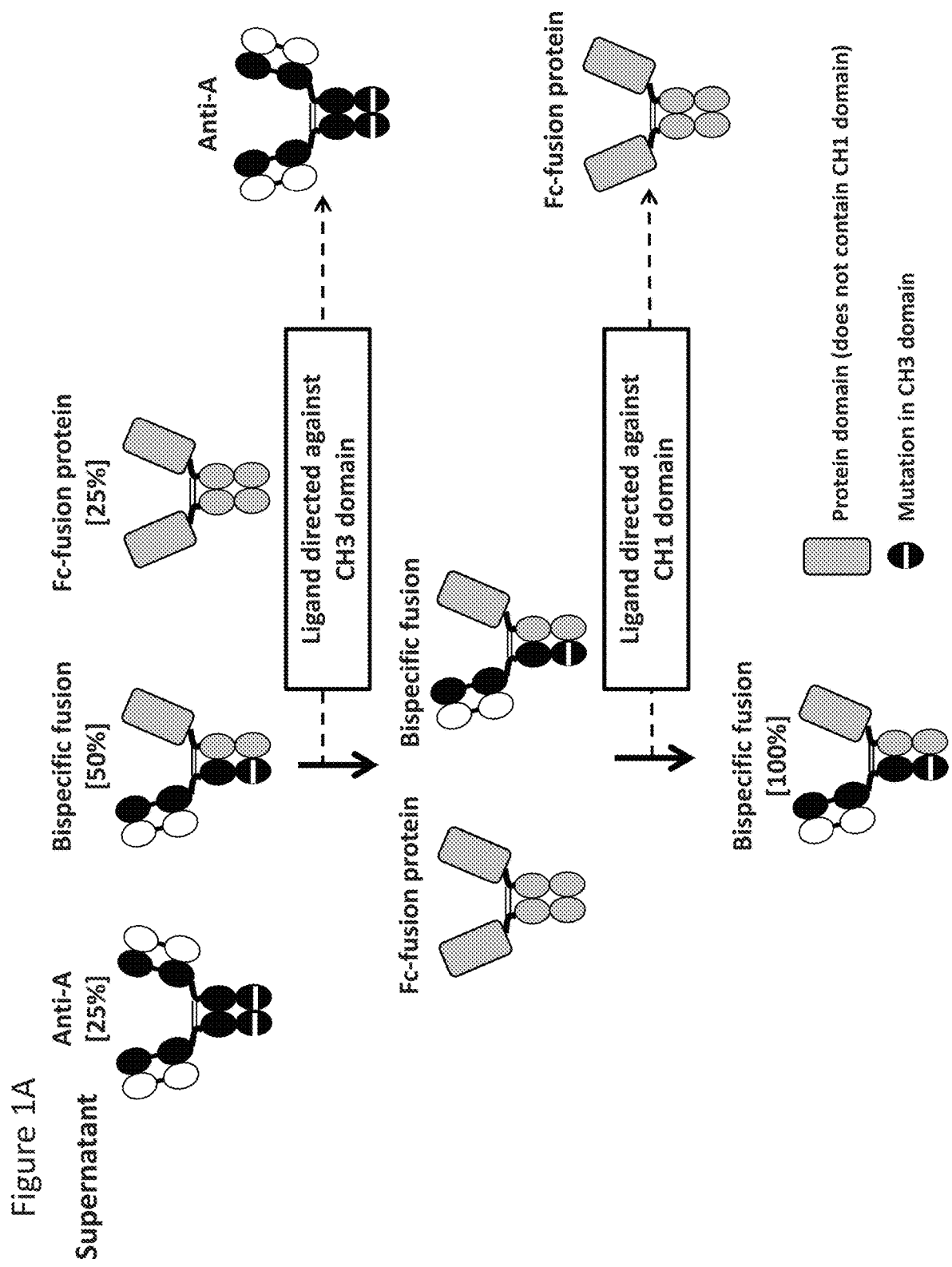
FIGS. 1A and 1B are a series of various embodiments of the purification processes of the disclosure.

Bispecific antigen-binding molecules such as bispecific antibodies have unique modes of action which are not enabled by monoclonal antibodies due to their ability to co-engage two different antigens. For example, retargeting of cytotoxic T-cells toward tumor cells by bispecific antibody is a successful strategy in therapeutic treatment of cancer which can't be mimicked by monoclonal antibody and mixture of monoclonal antibodies. In recent years, a very important number of bispecific antibody formats have been developed to address therapeutic opportunities. Desirable properties of these bispecific antibodies must be equivalent to monoclonal antibodies, i.e., in vitro and in vivo stability, minimal toxicity and immunogenicity, long-half life, ease of production and purification and, if needed, effector functions like ADCC and CDC. However, most bispecific antibody formats rely on highly engineered format which induces protein instability impacting antibody production and, potentially, immunogenicity. Ideally, the best bispecific antibody format should be as close as possible as WT natural IgG.

Production of bispecific antibodies using fully natural heavy and light chains could be potentially performed by co-expressing in a single cell one antibody heavy and light chains with different heavy and light chains from another antibody. However, this co-expression results in a mixture of antibody species where only a small fraction corresponds to the correct pairing of heavy and light chains which forms the hetero-dimer having the expected activity. In addition, the hetero-dimer is virtually undistinguishable from other antibody species and therefore can't be isolated and purified using classical purification approach. Several examples of formats that attempt to address these problems are described below.

To allow the isolation of bispecific antibody using conventional purification method, a mouse and a rat monoclonal antibody hybrid has been developed, and relies on a modification of conventional Protein A affinity chromatography. (see, e.g., Lindhofer, H. et al. (1995) J. Immunol. 155:219-225)). In this format, a mouse IgG2a and a rat IgG2b antibody are produced together in the same cell (e.g., either as a quadroma fusion of two hybridomas, or in engineered CHO cells). Because the light chains of each antibody associate preferentially with the heavy chains of their cognate species, only three distinct species of antibody can be assembled: the two parental antibodies, and a heterodimer of the two antibodies comprising one heavy/light chain pair of each, associating via their Fc portions. The desired heterodimer can be easily purified from this mixture because its binding properties to Protein A are different from those of the parental antibodies: rat IgG2b does not bind to protein A, whereas the mouse IgG2a does. Consequently, the mouse-rat heterodimer binds to Protein A but elutes at a higher pH than the mouse IgG2a homodimer, and this makes selective purification of the bispecific heterodimer possible. This hybrid format has two monovalent antigen binding sites. However, this format suffers from several limitations. One of its major disadvantages is that it is a mouse/rat hybrid which can be potentially highly immunogenic in human. In addition, antibody production using quadroma is limited due to its poor productivity.

To avoid mispairing problem of heavy and light chains when two different heavy chains are co-expressed with two different light chains in single cell, bispecific antibody format relying on a single light chain which could associate with two different heavy chains has been developed (Regeneron). In this format, transgenic mice have been generated by introducing in their genomes the human heavy chain repertoire with only one gene encoding for a single human light chain. This biased repertoire allow the generation of antibodies with different heavy chains but a common light chain. After isolation of parental antibodies with two different specificities, bispecific antibody can be easily assembled by co-expressing in a single cell two different heavy chains with a common light chain. With this approach, only three distinct species of antibody can be generated: the two parental antibodies, and a heterodimer comprising two different heavy chains and the common light chain corresponding to the bispecific antibody. To conveniently isolate this bispecific antibody, residues from IgG3 which disrupts binding of this isotype to Protein A are introduced in one heavy chain. Therefore, as the three antibody species have different affinity to Protein A, bispecific antibody can be selectively purified using Protein A affinity chromatography because the bispecific heterodimer (IgG1/IgG3) binds to Protein A but elutes at a higher pH than the WT homodimer (IgG3/IgG3). Like the mouse/rat heterodimer format, this format relies on asymmetric purification to isolate bispecific antibody from a mixture of antibodies and the final heterodimer has two different monovalent binding sites. This format, despite the advantages of being fully human and compatible with large-scale manufacturing, has also some limitations. Effectively, this bispecific format does not allow flexibility concerning the common light chain which can limit the epitope coverage accessible to these antibodies and rules-out the possibility of using existing antibodies. In addition, one of its major limitations is that some human VH germlines (IGHV3) has intrinsic affinity to protein A which can render bispecific antibody isolation using protein A chromatography ineffective. Moreover, the IgG3 mutations are located at the interface between the CH2 and CH3 domains, a region known to be important for binding to FcRn a major actor of IgG1 antibody half-life. This bispecific format may have altered pharmacokinetic properties compared to natural IgG1 antibodies.

The bispecific antigen-binding polypeptides of the disclosure, such as, for example, the bispecific antibodies described herein, overcome the disadvantages of other bispecific antibody formats. Effectively, they are fully human and involve a lack of a CH1 domain and a modification of the CH3 domain or modifications of the CH1 and CH3 domains which alter their binding capacity to a CH1 specific affinity chromatography media and to a CH3 affinity chromatography media to allow convenient isolation of bispecific antigen-binding polypeptides such as bispecific antibodies. The CH1 region of antibodies is not known to be involved in interactions with receptors or other proteins, and thus the effector and pharmacokinetic properties of the bispecific format of the invention remain unaltered. Similarly, the studies presented herein have identified in the CH3 domain, an epitope for a CH3 affinity chromatography media that is different of the epitope to Protein A. This epitope is neither involved in binding to FcRn nor to FcγRs and therefore does not change the effector and pharmacokinetic properties of the bispecific antibody compared to WT IgG1. In addition, the mutations introduced in CH1 and CH3 domain do not change antibody thermostability and productivity compared to WT IgG1.

EXAMPLES

The following examples are provided to describe to those of ordinary skill in the art how to make and use methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Design of an Asymmetric Purification Strategy for Bispecific Antibodies

Figure 1B:
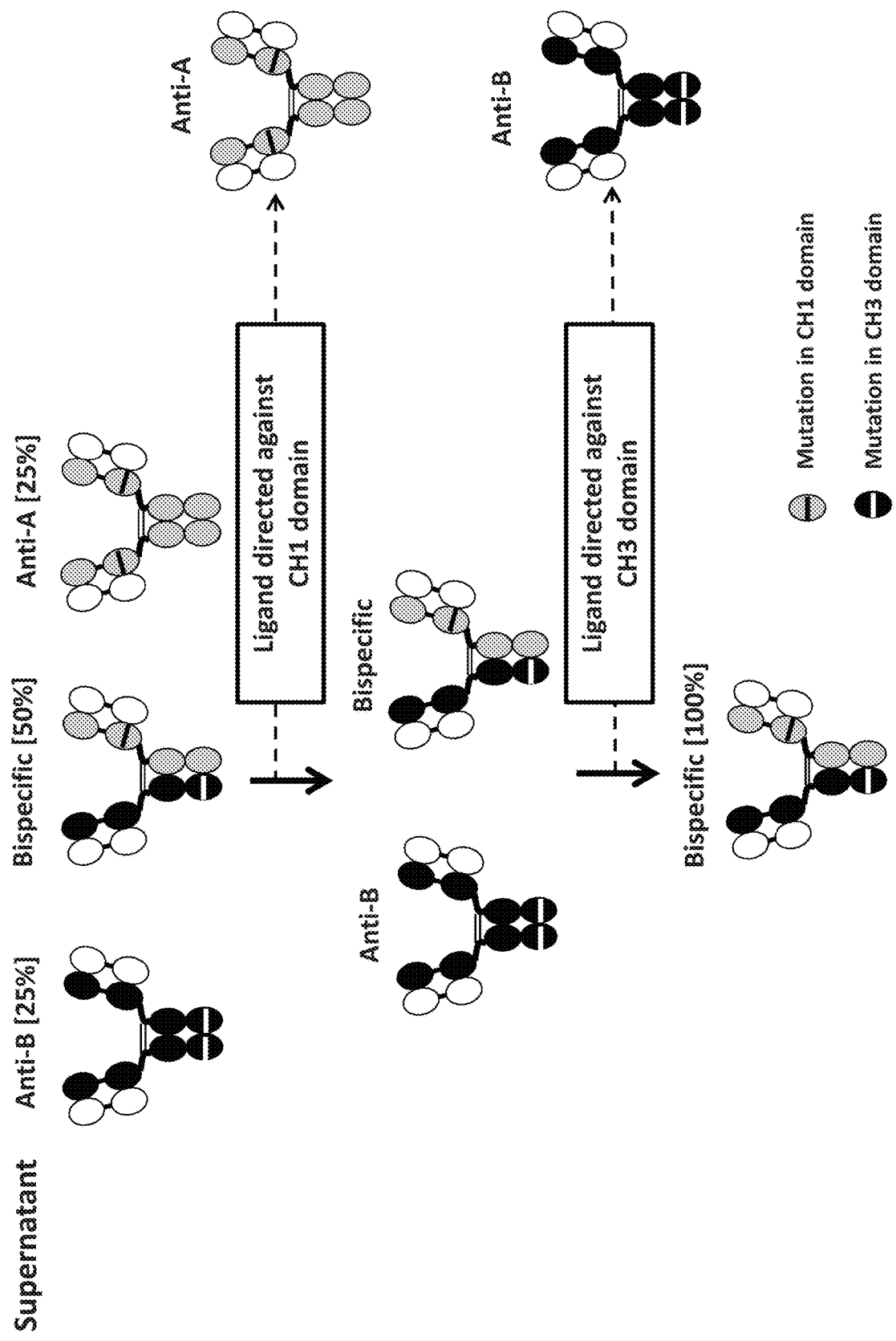

Bispecific antibody composed of two different heavy chains and one common light chain can be expressed by co-transfection of three different chains: two different heavy chains and one common light chain. A mixture of three antibodies will result from this co-transfection: two parental monoclonal antibodies and one bispecific heterodimeric antibody (FIG. 1). To specifically purify the bispecific antibody from the mixture, two-step asymmetric affinity purification can be used to isolate the antibody of interest. Effectively, specific ligands targeting immunoglobulin domains like the CH1 and CH3 domains of the IgG heavy chains can be developed for affinity purification. Mutations introduced in the epitopes of specific ligands can be further introduced the IgG CH1 and CH3 domains to abrogate IgG binding to these CH1 and CH3 affinity reagents. Alternatively, a polypeptide containing an epitope binding region and an IgG Fc region composed of CH2 and CH3 domains but devoid of any CH1 domain like scFv-Fc polypeptide could also be generated to abrogate binding to the CH1 affinity reagents. Therefore, a first affinity step, performed with ligand directed against CH1 domain, will only specifically isolate bispecific and monoclonal antibody having WT (i.e. non-mutated) CH1 domains. During this step, monoclonal antibody with HC dimer having two mutated CH1 domains or dimer composed of a polypeptide that do not contain a CH1 domain like scFv-Fc are eliminated in the flow-through as they do not bind to the CH1 specific ligand. Then, a second affinity step, performed with ligand directed against CH3 domain, allow the specific purification of the heterodimeric bispecific antibody as it contains one WT CH3 domain recognized by the affinity reagent. This last step removes monoclonal antibody with HC dimer having two mutated CH3 domains.

Example 2

Mutagenesis of CH1 and CH3 Domains

Mutations were introduced in the CHI (FIG. 2) and CH3 domain (FIG. 3) in order to abrogate binding to affinity reagents which are targeting these domains, the CaptureSelect® IgG-CH1 (aldehyde-activated agarose resin that specifically binds to human IgG-CH1 region) and the CaptureSelect® IgG Fc XL (aldehyde-activated agarose resin that specifically binds to human IgG-CH3 region), respectively. Single and double mutations were designed to either replace WT residue by alanine or by amino acids with longer and/or charged side chains like glutamine, glutamic acid, lysine and arginine. In addition, human IgG residues were also replaced by their equivalent murine IgG1 residues determined by sequence alignment between human and mouse IgG.

Figure 4:
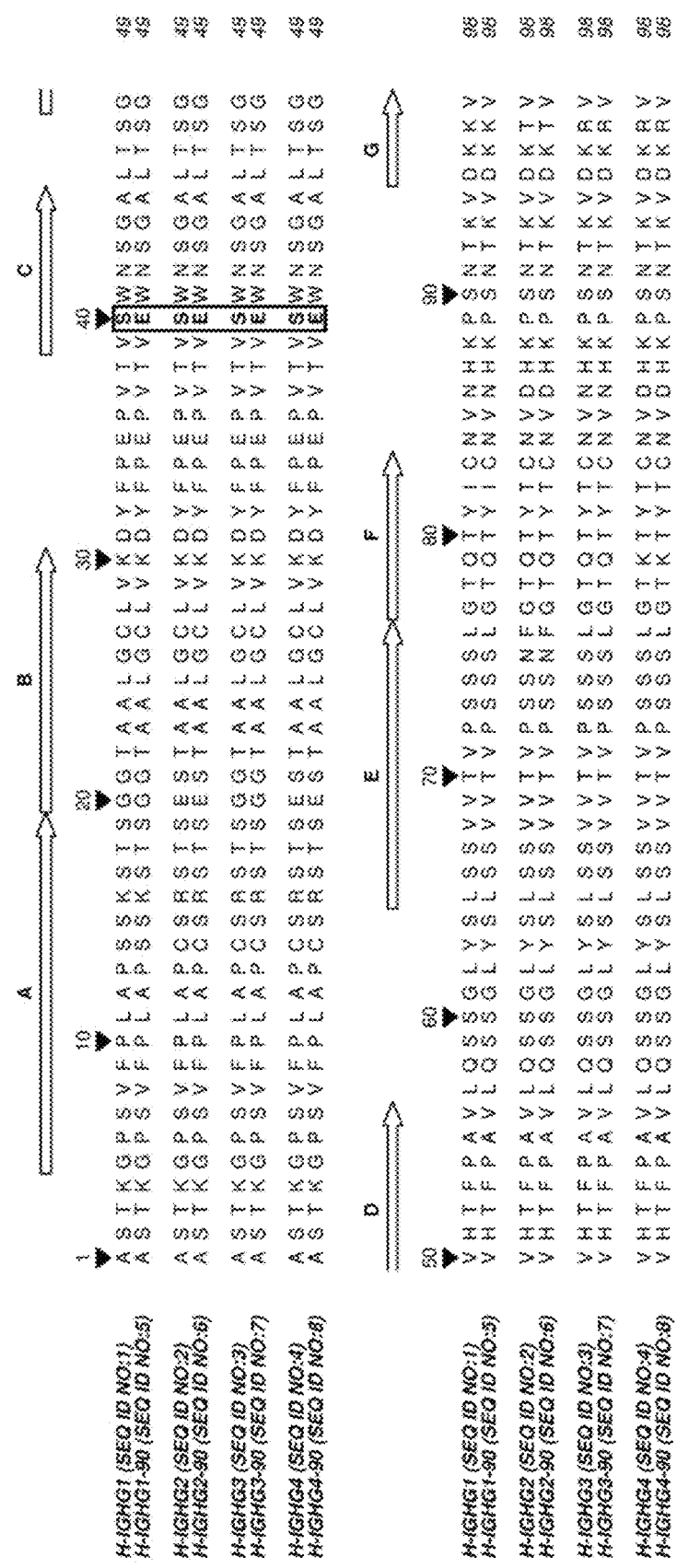
FIG. 4 is an illustration depicting the sequence alignment of the H-IGHG1 (SEQ ID NO: 1) CH1 domain and the H-IGHG1 90 (SEQ ID NO: 5) CH1 domain, where the H-IGHG1 90 mutant is a variant of the H-IGHG1 sequence having a glutamic acid at position 40 (also referred to herein as an S40E mutation); the H-IGHG2 (SEQ ID NO: 2) CH1 domain and the H-IGHG2 90 (SEQ ID NO: 6) CH1 domain, where the H-IGHG2 90 mutant is a variant of the H-IGHG2 sequence having a glutamic acid at position 40 (also referred to herein as an S40E mutation); the H-IGHG3 (SEQ ID NO: 3) CH1 domain and the H-IGHG3 90 (SEQ ID NO: 7) CH1 domain, where the H-IGHG3 90 mutant is a variant of the H-IGHG3 sequence having a glutamic acid at position 40 (also referred to herein as an S40E mutation); and the H-IGHG4 (SEQ ID NO: 4) CH1 domain and the H-IGHG4 90 (SEQ ID NO: 8) CH1 domain, where the H-IGHG4 90 mutant is a variant of the H-IGHG4 sequence having a glutamic acid at position 40 (also referred to herein as an S40E mutation).
Figure 5:
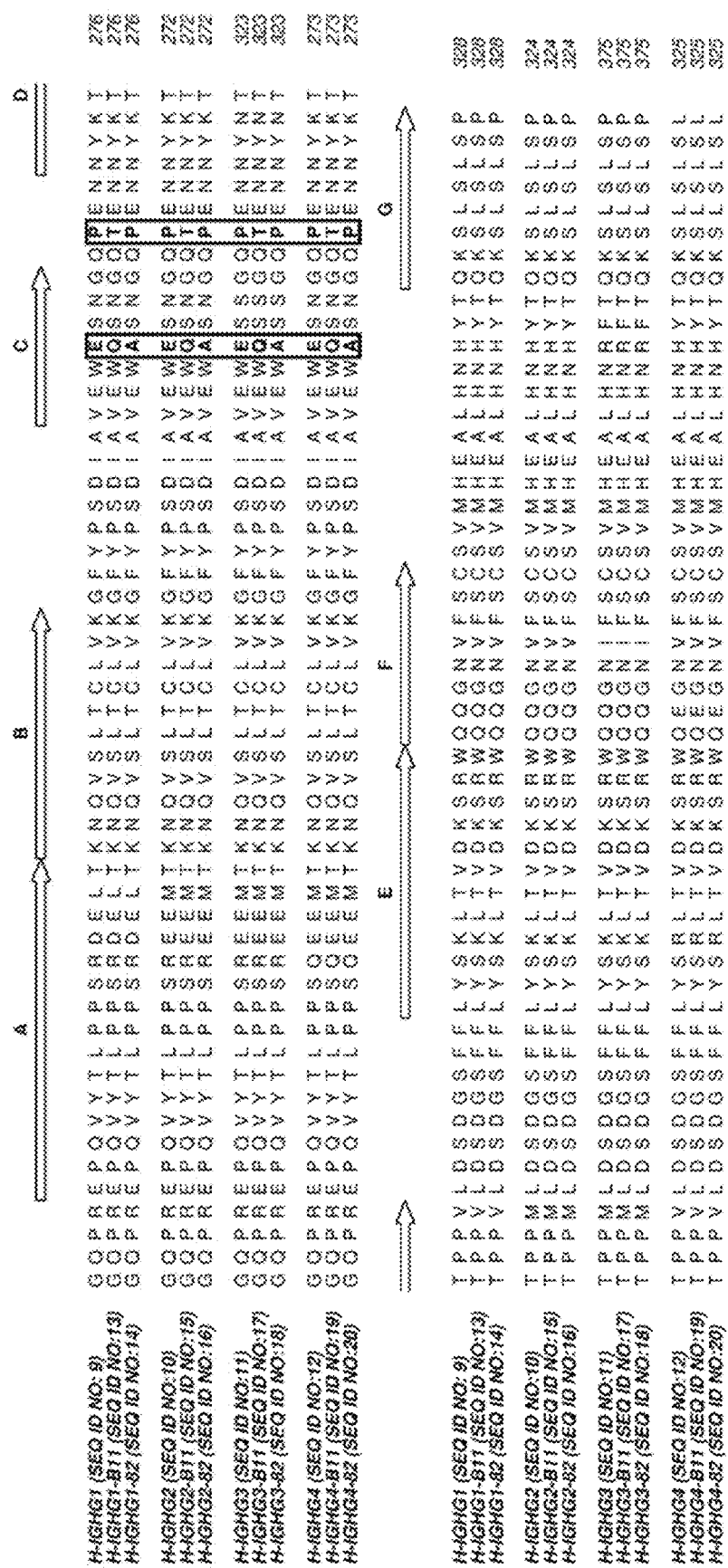
FIG. 5 is an illustration depicting the sequence alignment of the H-IGHG1 (SEQ ID NO: 9) CH3 domain and the H-IGHG1 B11 (SEQ ID NO: 13) CH3 domain and the H-IGHG1 82 (SEQ ID NO: 14) CH3 domain, where the H-IGHG1 B11 mutant is a variant of the H-IGHG1 sequence having a glutamine at position 265 (also referred to herein as an E265Q mutation) and a threonine at position 270 (also referred to herein as an P270T mutation) and where the H-IGHG1 82 mutant is a variant of the H-IGHG1 sequence having a alanine at position 265 (also referred to herein as an E265A mutation); the H-IGHG2 (SEQ ID NO: 10) CH3 domain and the H-IGHG2 B11 (SEQ ID NO: 15) CH3 domain and the H-IGHG2 82 (SEQ ID NO: 16) CH3 domain, where the H-IGHG2 B11 mutant is a variant of the H-IGHG2 sequence having a glutamine at position 261 (also referred to herein as an E261Q mutation) and a threonine at position 266 (also referred to herein as an P266T mutation) and where the H-IGHG2 82 mutant is a variant of the H-IGHG2 sequence having a alanine at position 261 (also referred to herein as an E261A mutation); the H-IGHG3 (SEQ ID NO: 11) CH3 domain and the H-IGHG3 B11 (SEQ ID NO: 17) CH3 domain and the H-IGHG3 82 (SEQ ID NO: 18) CH3 domain, where the H-IGHG3 B11 mutant is a variant of the H-IGHG3 sequence having a glutamine at position 312 (also referred to herein as an E312Q mutation) and a threonine at position 317 (also referred to herein as an P317T mutation) and where the H-IGHG3 82 mutant is a variant of the H-IGHG3 sequence having a alanine at position 312 (also referred to herein as an E312A mutation); and the H-IGHG4 (SEQ ID NO: 12) CH3 domain and the H-IGHG4 B11 (SEQ ID NO: 19) CH3 domain and the H-IGHG4 82 (SEQ ID NO: 20) CH3 domain, where the H-IGHG4 B11 mutant is a variant of the H-IGHG4 sequence having a glutamine at position 262 (also referred to herein as an E262Q mutation) and a threonine at position 267 (also referred to herein as an P267T mutation) and where the H-IGHG4 82 mutant is a variant of the H-IGHG4 sequence having a alanine at position 262 (also referred to herein as an E262A mutation).
Figure 6:
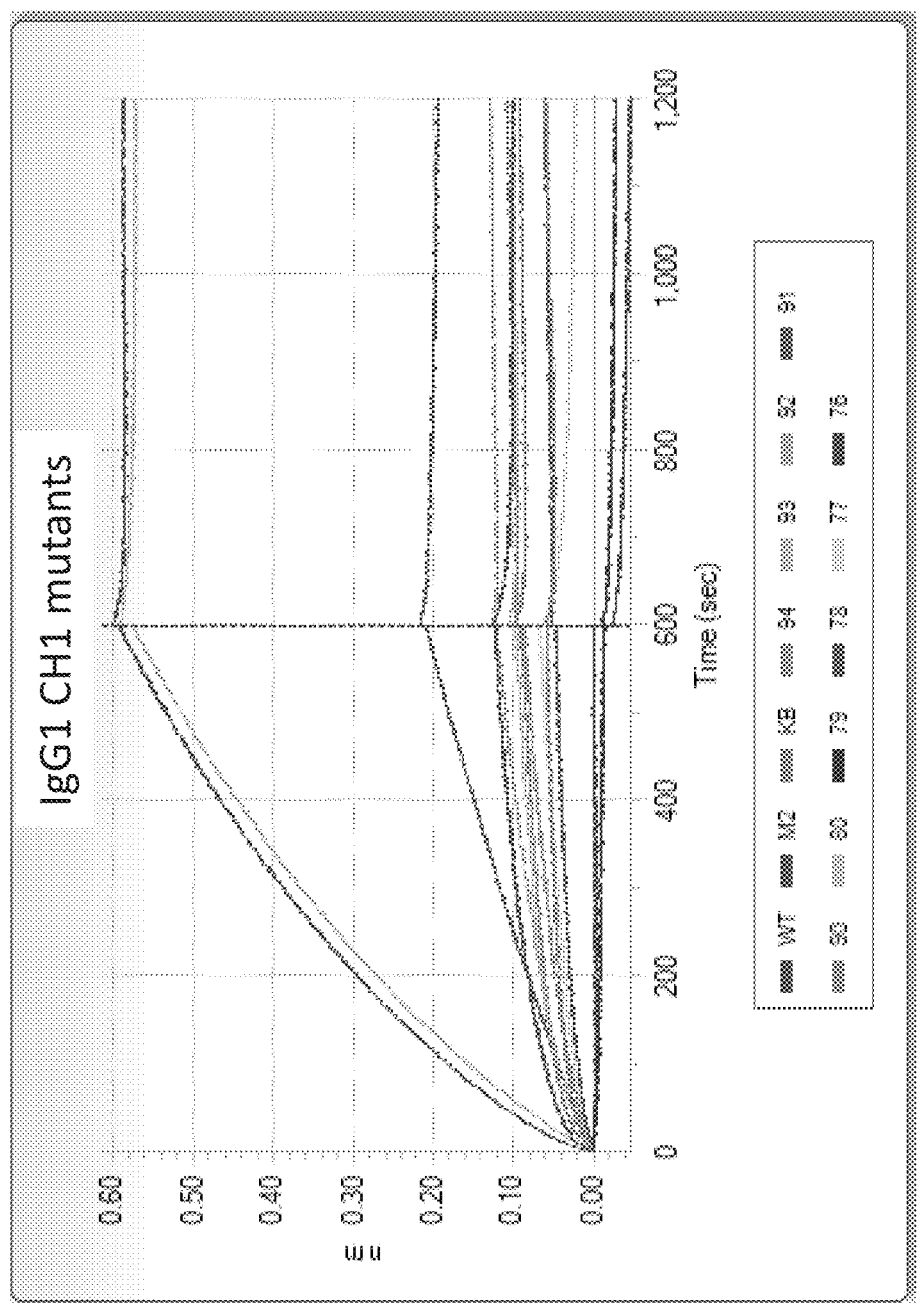
FIG. 6 is a graph depicting the binding of IgG1 antibodies mutated in the CH1 domain with the ligand of a CH1 specific chromatography media as determined with the OCTET technology.
Figure 7:
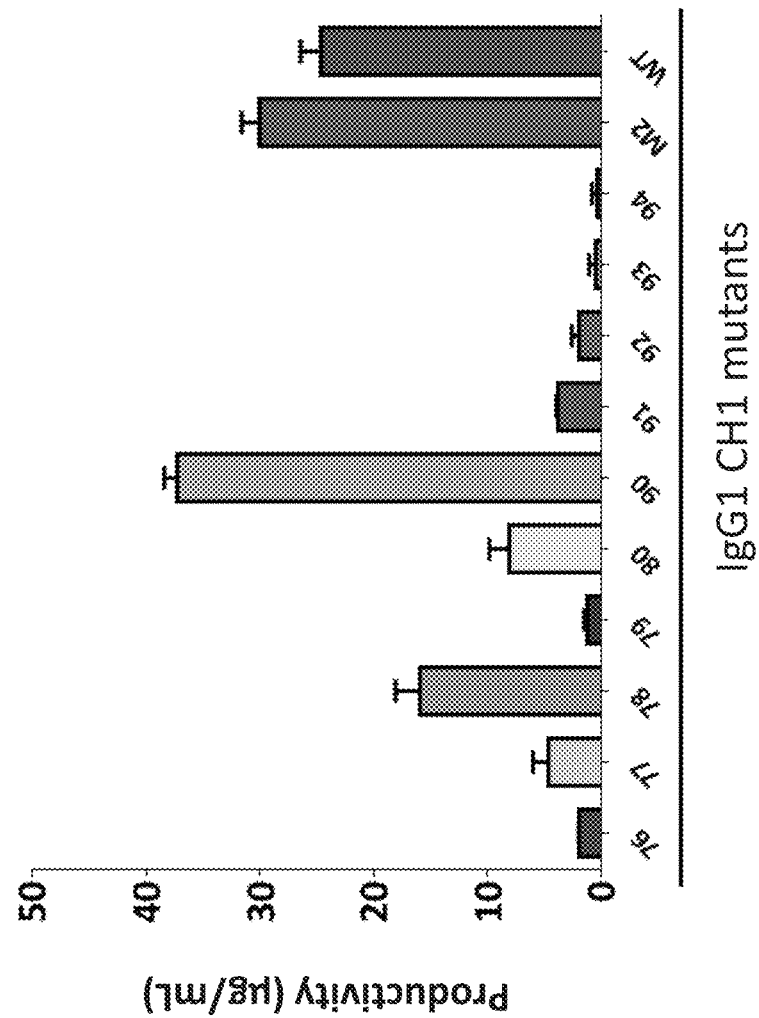
FIG. 7 is a graph indicating the concentration of WT IgG1 antibody and IgG1 antibodies mutated in the CH1 domain obtained in the supernatant of producing cells after capture with Protein A biosensor using the OCTET technology.
Figure 8:
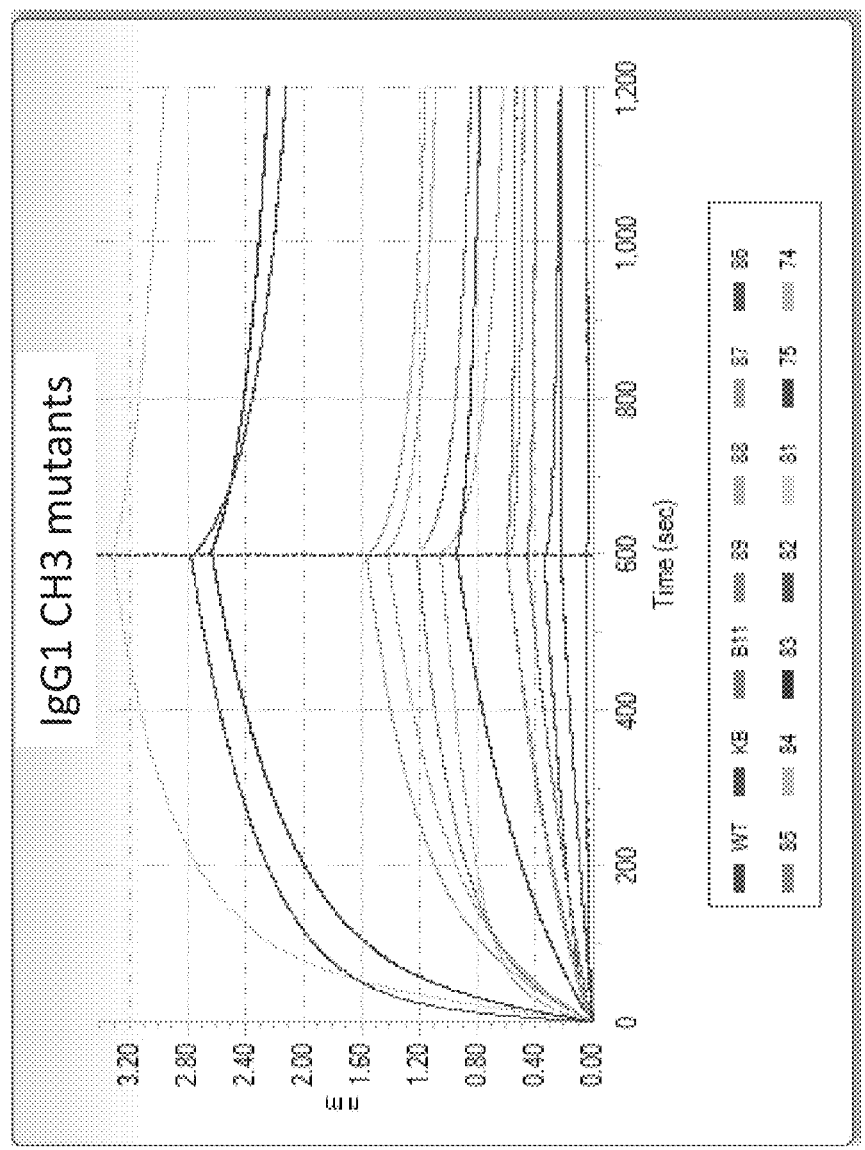
FIG. 8 is a graph depicting the binding of IgG1 antibodies mutated in the CH3 domain with the ligand of a CH3 specific chromatography media as determined with the OCTET technology.
Figure 9:
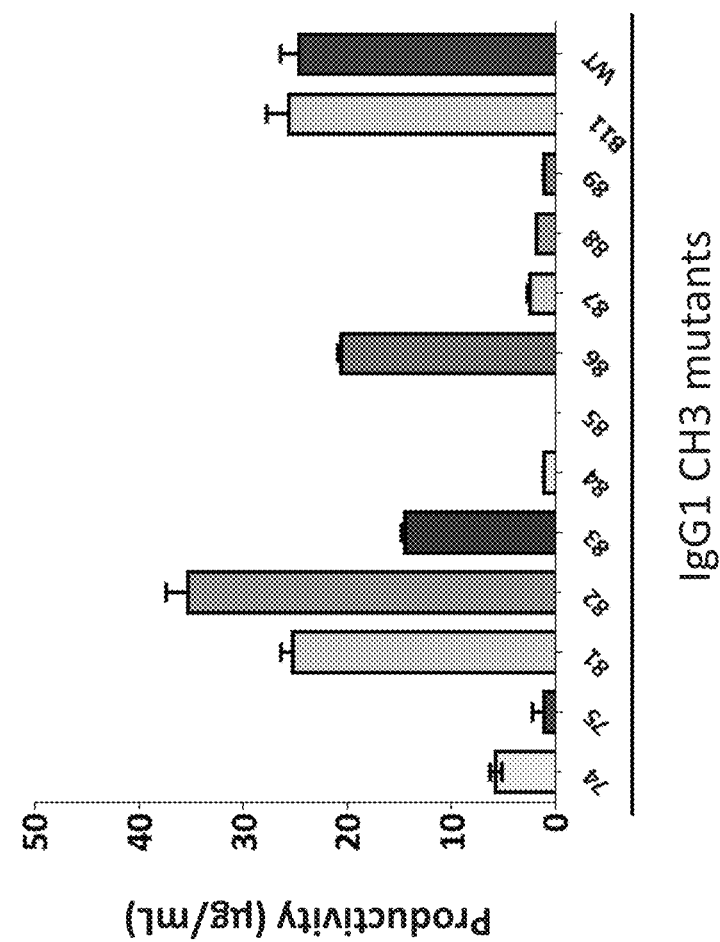
FIG. 9 is a graph indicating the concentration of WT IgG1 antibody and IgG1 antibodies mutated in the CH3 domain obtained in the supernatant of producing cells after capture with Protein A biosensor using the OCTET technology.
Figure 10:
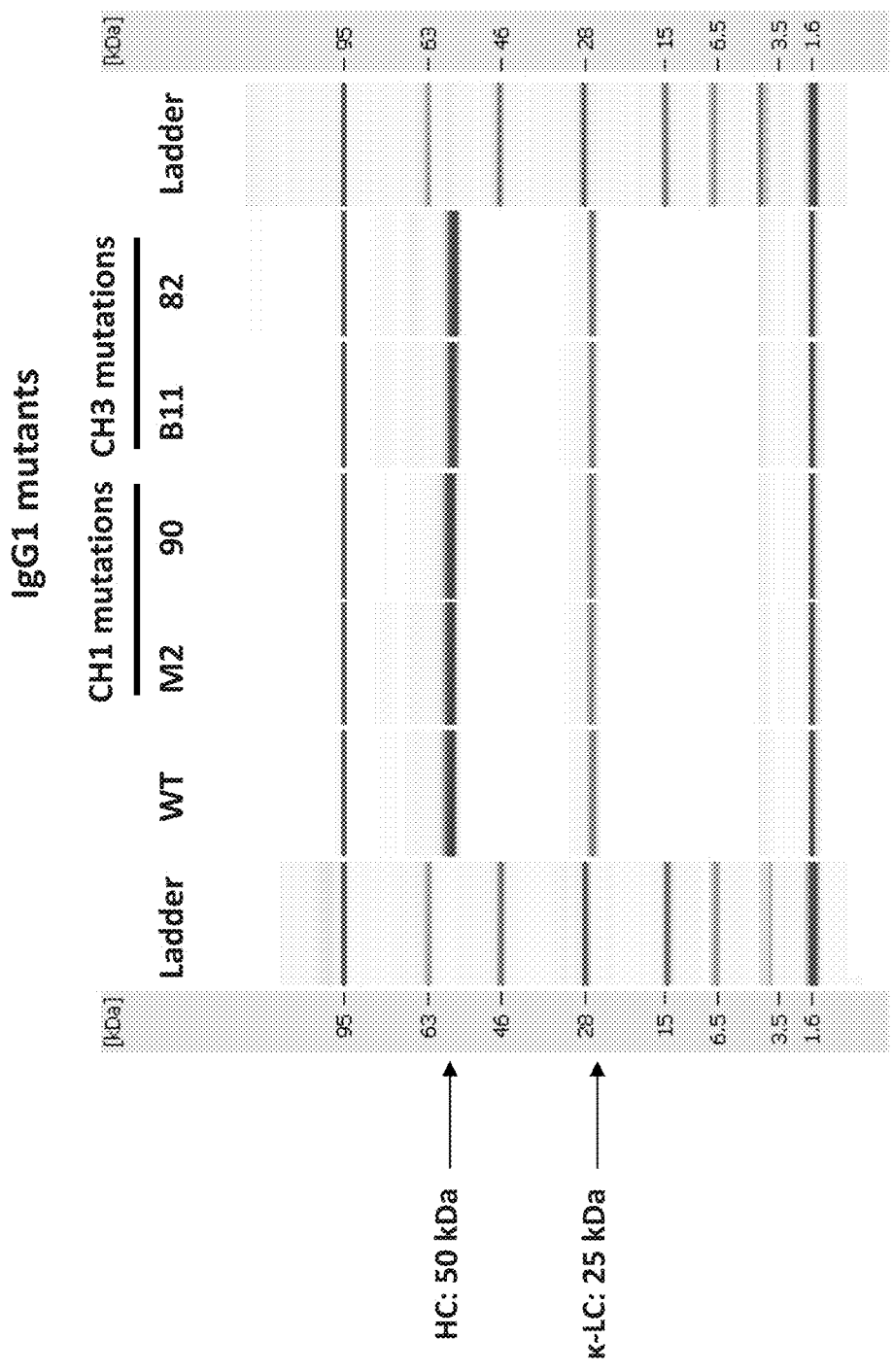
FIG. 10 is gel-like image representation of an Agilent protein 230 chip run monitoring the IgG1 CH1 and CH3 mutant's size in reducing and denaturing conditions.
Figure 11:
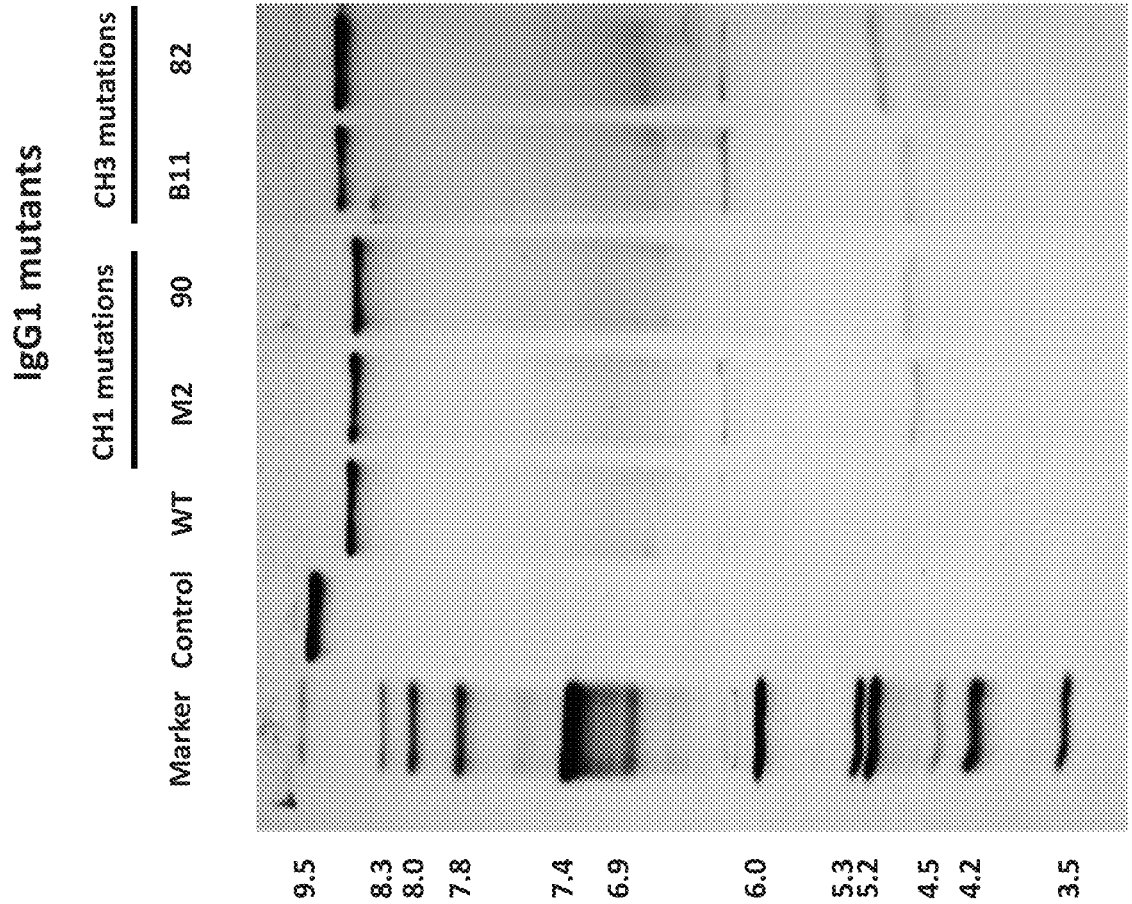
FIG. 11 is an isoelectric focusing polyacrylamide gel of the IgG1 CH1 and CH3 mutants to monitor antibody isoelectric point.
Figure 12:
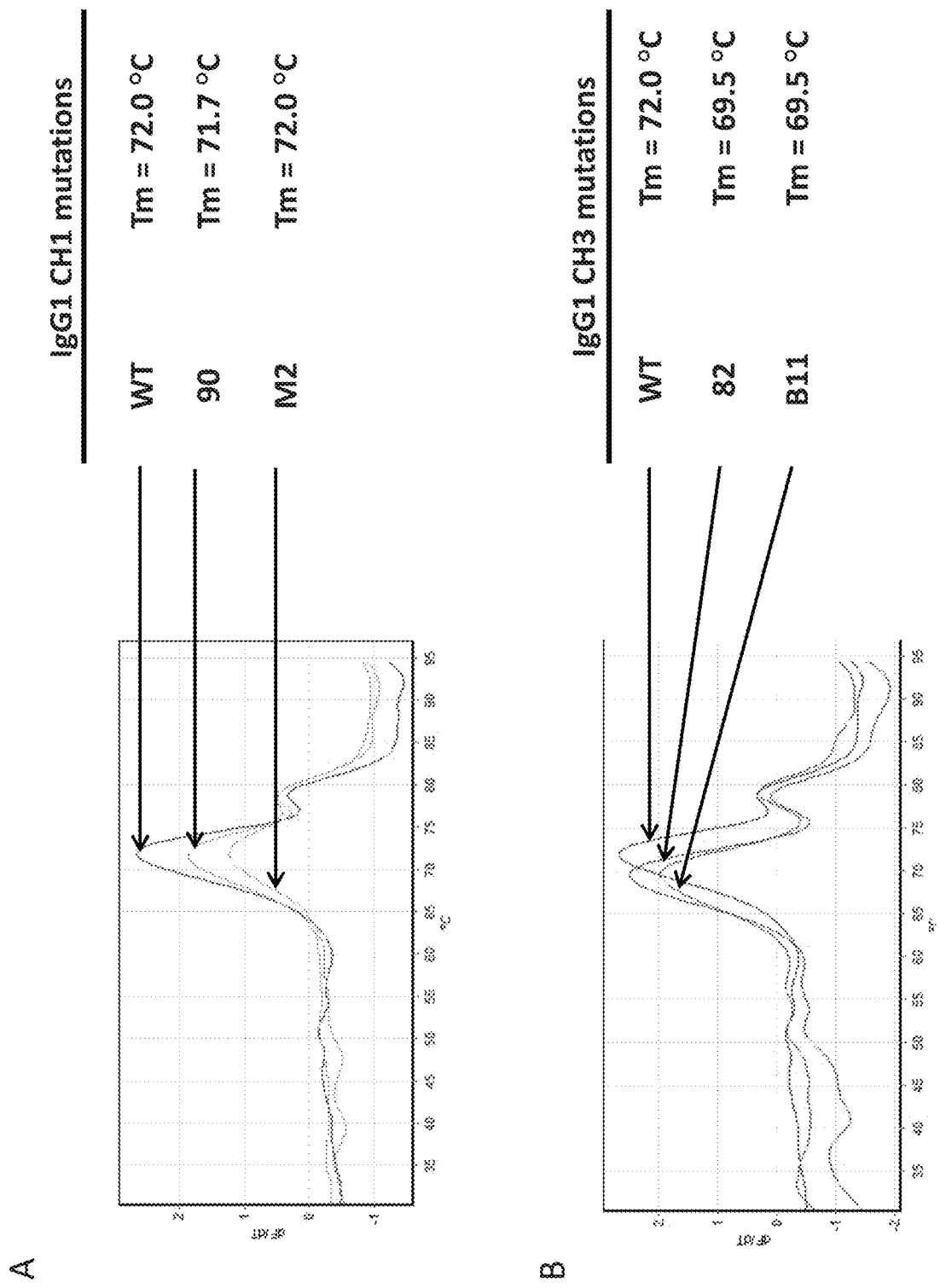
FIGS. 12A and 12B are a series of graphs showing the thermal stability of IgG1 CH1 mutants compared to WT IgG1 (FIG. 12A) and IgG1 CH3 mutants compared to WT IgG1 (FIG. 12B) determined by differential scanning fluorimetry.

Single and double mutations in CH1 domain and CH3 domain of human IgG1, IgG2, IgG3 and IgG4 are indicated in sequence alignments represented in FIG. 4 and FIG. 5, respectively. These mutations are located in the C n-strand and the CD loop (according to IMGT nomenclature) of the CH1 and CH3 immunoglobulin domains of human IgG1, IgG2, IgG3 and IgG4. More precisely, these mutations are at position 40 in the CH1 domain of human IgG1, IgG2, IgG3 and IgG4 and at position 265, 261, 312 and 262 in the CH3 domains of IgG1, IgG2, IgG3 and IgG4, respectively.

Example 3

Characterization of IgG1 CH1 Mutants

To determine if mutations introduced in the CH1 domain could abrogate binding to the CaptureSelect® IgG-CH1 resin, a screen was performed using Octet technology to measure the interaction of IgG1 variants with CaptureSelect® IgG-CH1 ligand. Streptavidin biosensors were coated with biotinylated CaptureSelect® IgG-CH1 ligand and variants of the IgG1 having mutations described in FIG. 2 were expressed in mammalian cells, purified using protein A and used at a normalized concentration of 10 g/ml. Several mutations in the CH1 domain led to significant reduction of the IgG binding to the ligand of the CaptureSelect® IgG-CH1 resin compared to WT IgG as shown on the sensorgram in FIG. 6. Indeed, at the exception of the mutant 93, modifications at positions 40 and 47 of the IgG CH1 domain decrease antibody association to the ligand of the CaptureSelect® IgG-CH1 resin. In parallel, antibody variants productivity was also monitored using Octet technology to determine if mutations introduced in the CH1 domain could affect the normal expression of the IgG. The biosensors were coated with protein A to capture IgGs and to determine their concentration in the cell supernatant. Amongst mutants with reduced binding to the IgG-CH1 ligand, only the 90 and M2 mutants having CH1 mutation(s) (FIG. 7) are produced at the same level as the WT IgG.

Example 4

Characterization of IgG1 CH3 Mutants

To determine if mutations introduced in the CH3 domain could abrogate binding to the CaptureSelect® IgG-FcXL resin, a screen was performed using Octet technology to measure the interaction of IgG variants with CaptureSelect® IgG-FcXL ligand. Streptavidin biosensors were coated with biotinylated CaptureSelect® IgG-FcXL ligand and variants of the IgG1 having mutations described in FIG. 3 were expressed in mammalian cells, purified using protein A and used at a normalized concentration of 10 μg/ml. Several mutations in the CH3 domain led to significant reduction of the IgG binding to the ligand of the CaptureSelect® IgG-FcXL resin compared to WT IgG as shown on the sensorgram in FIG. 8. Indeed, at the exception of the mutations 81 and 83, modifications at positions 265, 266 and 270 of the IgG CH3 domain decrease antibody association to the ligand of the CaptureSelect® IgG-FcXL resin. In parallel, antibody variants productivity was also monitored using Octet technology to determine if mutations introduced in the CH3 domain could affect the normal expression of the IgG. The biosensors were coated with protein A to capture IgGs and to determine their concentration in the cell supernatant. Amongst mutants with reduced binding to the IgG-FcXL ligand, only the 82 and B11 mutants carrying CH3 mutation(s) (FIG. 9) are produced at the same level as the WT IgG.

Example 5

Quality Controls of CH1 and CH3 Modified IgG1 Antibodies

To control the quality of IgG1 products carrying mutations 82, B11, 90 and M2, samples of purified IgG variants were analyzed in reducing and denaturing conditions using the Agilent 2100 Bioanalyzer. The same profile between the selected mutants and the WT IgG was obtained as observed in FIG. 10. Indeed, two bands corresponding to the heavy chains and to the light chains were observed at the expected sizes of 50 kDa and 25 kDa respectively. No impurity was detected for all samples tested. These proteins were further analyzed by isoelectric focusing (IEF) to determine their charge homogeneity. Homogeneous bands corresponding to the antibody product were observed at the expected pI (FIG. 11). CH1 mutants M2 and 90 have the same pI than the WT Ab (pI equal at 8.50), while CH3 mutants B11 and 82, which have more positive charges because one glutamic acid (E) residue, has been replaced by a neutral residue, have pI equal at 8.58.

Example 6

Determination of the Impact of CH1 and CH3 Mutations on IgG1 Thermal Stability To determine if mutations introduced in the CH1 and CH3 domains were affecting IgG1 antibody thermal stability, the four selected mutants were analyzed using differential scanning fluorimetry (DSF) technology and compared to the WT antibody. $T_m$ measured for CH1 mutations were equivalent to the $T_m$ of the WT Ab, 71.7° C. and 72.0° C. for the 90 and M2 mutants, respectively (FIG. 12A). Thus, the thermal stability of the IgG1 was maintained with mutations in the IgG CH1 domain. CH3 mutations 82 and B11 induce a slight decrease of 2° C. of the thermal stability of whole IgG as seen in FIG. 12B. However, this small $T_m$ reduction is acceptable as it is within the range of thermal stabilities observed between IgG1 and IgG4 subclasses (Garber and Demarest, BBRC, 2007).

Example 7

Figure 13:
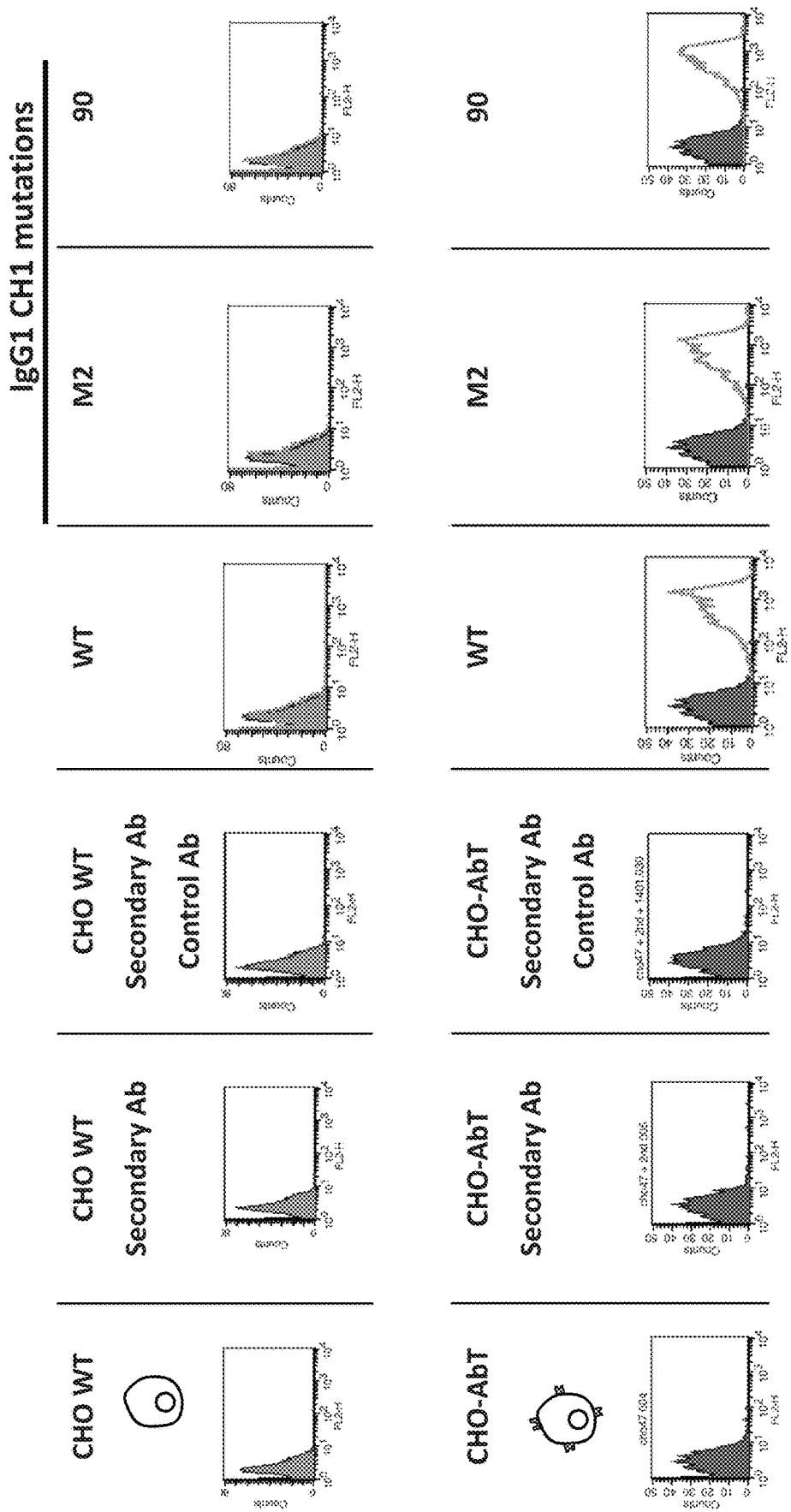
FIG. 13 shows the specific functional binding properties of IgG1 CH1 mutants on cells expressing their antibody target (AbT) as determined by FACS.
Figure 14:
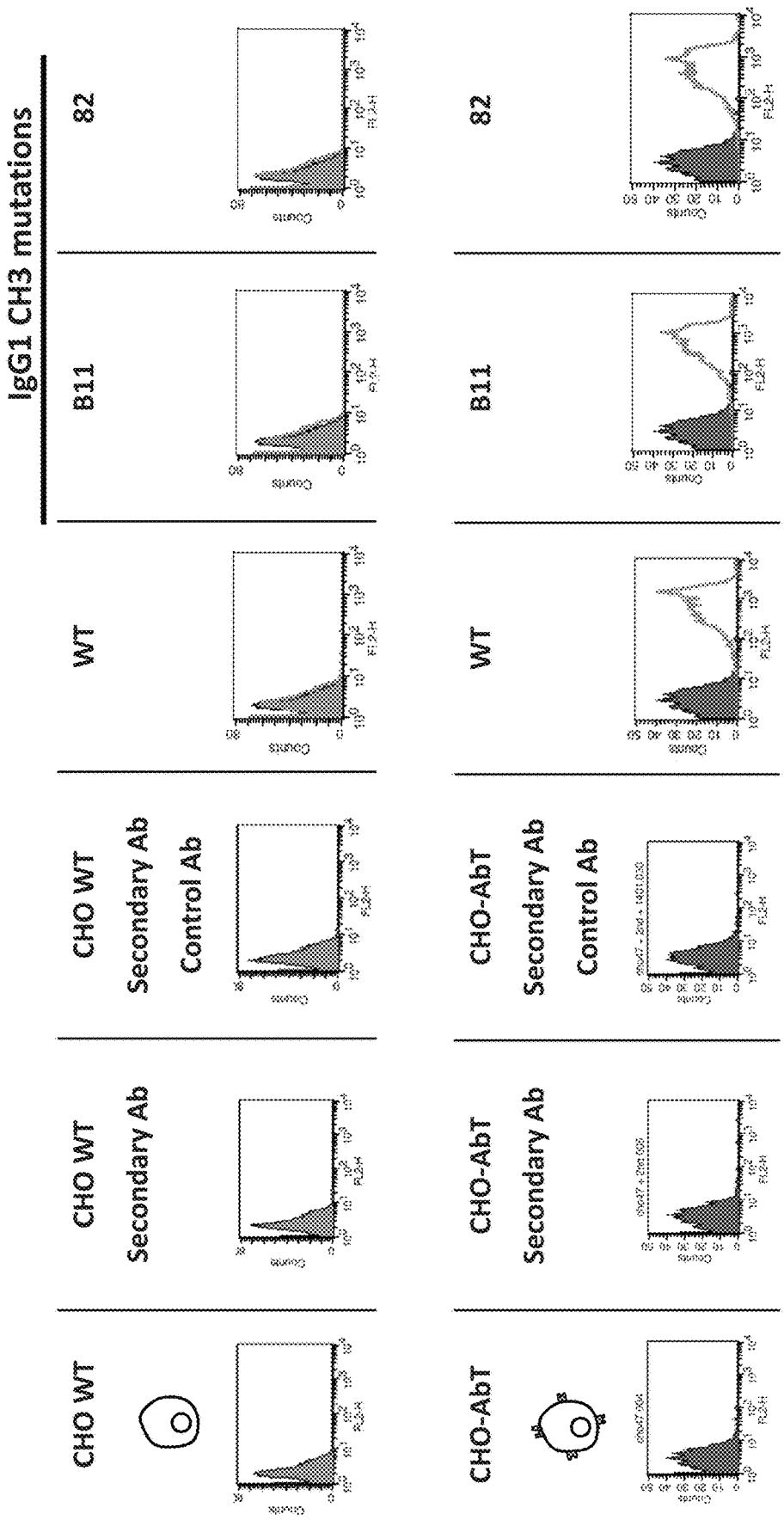
FIG. 14 shows the specific functional binding properties of IgG1 CH3 mutants on cells expressing their antibody target (AbT) as determined by FACS.

Determination of the Impact of CH1 and CH3 Mutations on IgG1 Binding Properties The major biological function of an IgG is its antigen-binding activity. Therefore, FACS analyses were performed to verify that the antibody engineering, corresponding to the introduction of mutations in the CH1 and CH3 domains, did not alter the IgG biological function. No nonspecific interaction of IgG1 CH1 and CH3 mutants could be detected with CHO WT cells (FIGS. 13 and 14, upper panel) as no fluorescence intensity shift between the mutants and the negative control were detected on negative cells (CHO WT cells). Moreover, specific IgG binding on CHO cells expressing antibody target was confirmed for both CH1 and CH3 mutants (FIGS. 13 and 14, lower panel) indicating that IgG biological function was conserved for all mutants, as similar shift of fluorescence intensity was monitored for the WT and mutated forms of the antibody on cells which specifically express the antibody target (CHO-AbT cells).

Example 8

Figure 15:
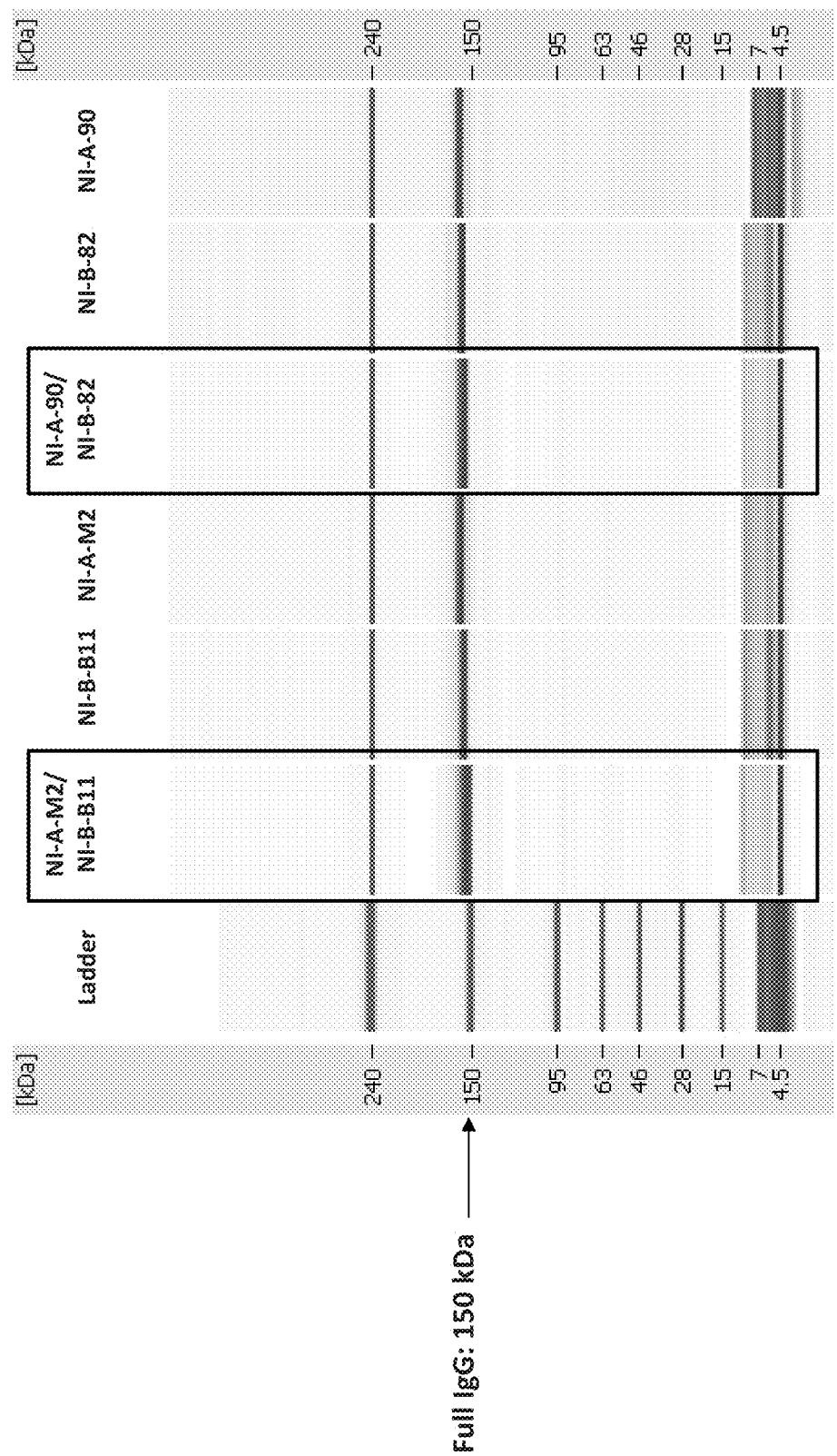
FIG. 15 is gel-like image representation of an Agilent protein 230 chip run monitoring the parental monoclonal CH1 and CH3 mutant's size as well as bispecific antibodies in denaturing conditions and non-reducing conditions. Bispecific products are highlighted by boxes.
Figure 16:
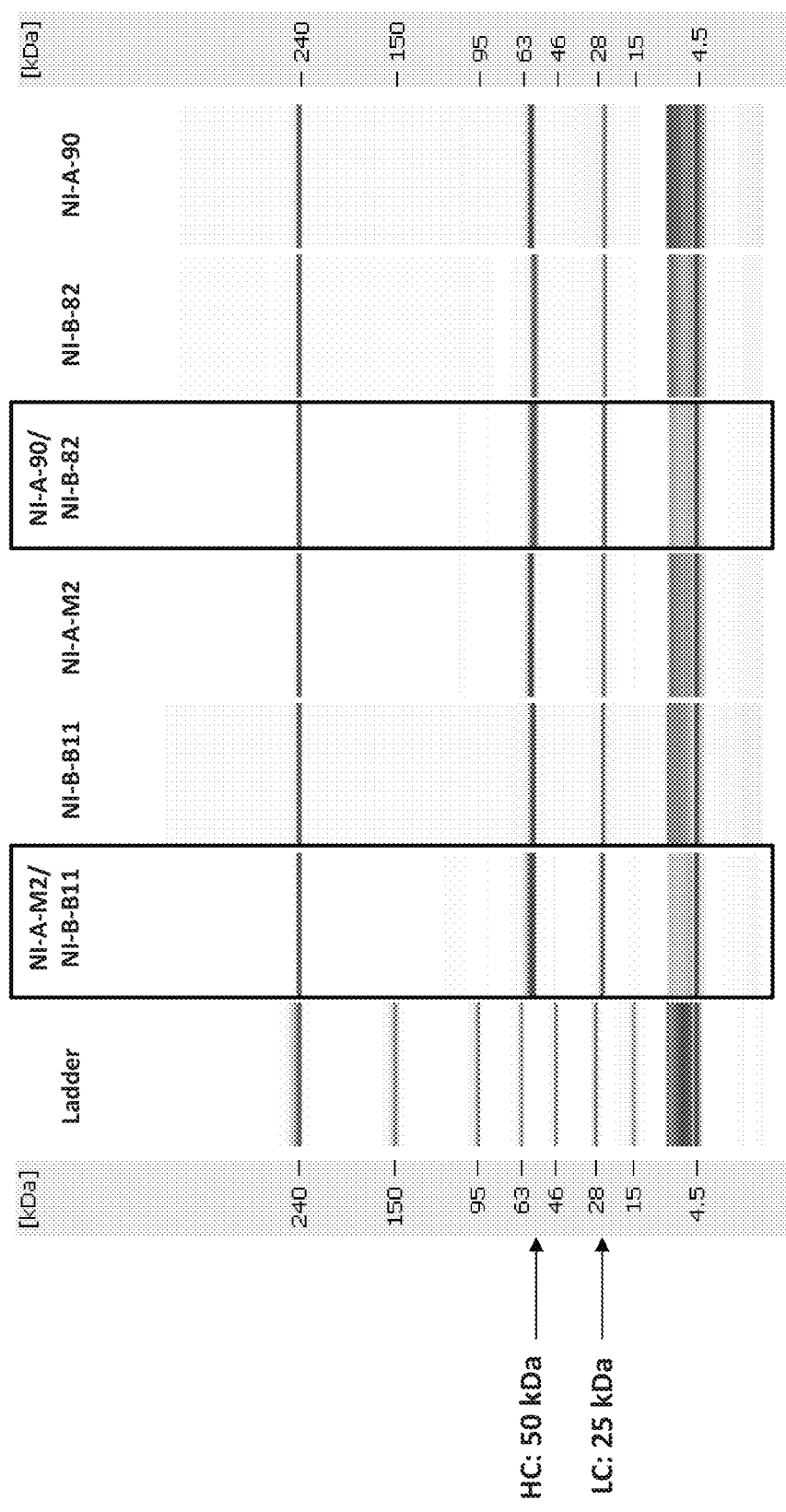
FIG. 16 is gel-like image representation of a protein 230 chip run monitoring the parental monoclonal CH1 and CH3 mutant's size as well as bispecific antibodies in denaturing and reducing conditions. Bispecific products are highlighted by boxes.

Production and Asymmetric Purification of Bispecific IgG Having One Common Light Chain and Two Different Heavy Chains Respectively Modified in their CH1 and CH3 Domains To establish a proof-of-concept, a bispecific antibody having one common LC and two different HCs with two different specificities must be used. Two Abs, NI-A and NI-B, share a common LC but bind distinct antigens. The NI-A binds to human CD3 and the NI-B binds to human IL-17. The selected CH1 and CH3 mutation(s) were introduced into expression vectors encoding the NI-A and NI-B antibodies, respectively. Afterward, a transient co-transfection was performed in mammalian cell with two vectors encoded the NI-A and the NI-B antibodies in order to generate a mixture of 3 antibodies, two parental monospecific forms and one bispecific form. Two bsAbs have been produced in parallel: one carrying the single mutations, called NI-A-90/NI-B-82, and the other one having the double mutations, named NI-A-M2/NI-B-B11. Bispecific antibodies were then purified and isolated from the supernatant by performing the two-steps asymmetric purification process using the Capture Select IgG-CH1 and then CaptureSelect IgG-Fc XL affinity matrix. In parallel to the two-step process, a protein A purification was performed on aliquot of supernatant containing the antibody mixture to isolate the three different species. A gel analysis in non-reducing and denaturing conditions was performed by using the Agilent 2100 Bioanalyzer. One band at the expected size (150 kDa) was obtained for each bispecific antibodies and its parental monoclonal antibodies (FIG. 15). In parallel, a gel analysis in reducing and denaturing conditions was performed (FIG. 16). Two bands are detected for each bispecific antibodies and parental monoclonal antibodies: one at 25 kDa and one at 50 kDa corresponding to the light chain and the heavy chain, respectively. Three bands were expected for bispecific antibodies, the first at 25 kDa for LCs, the second at 52,170 kDa for the HC of the NI-A and the third at 52,370 KDa for the HC of the NI-B. However, due to the very small difference in molecular weight, two bands corresponding to two different heavy chains cannot be resolved using the Agilent 2100 Bioanalyzer technology.

Figure 17:
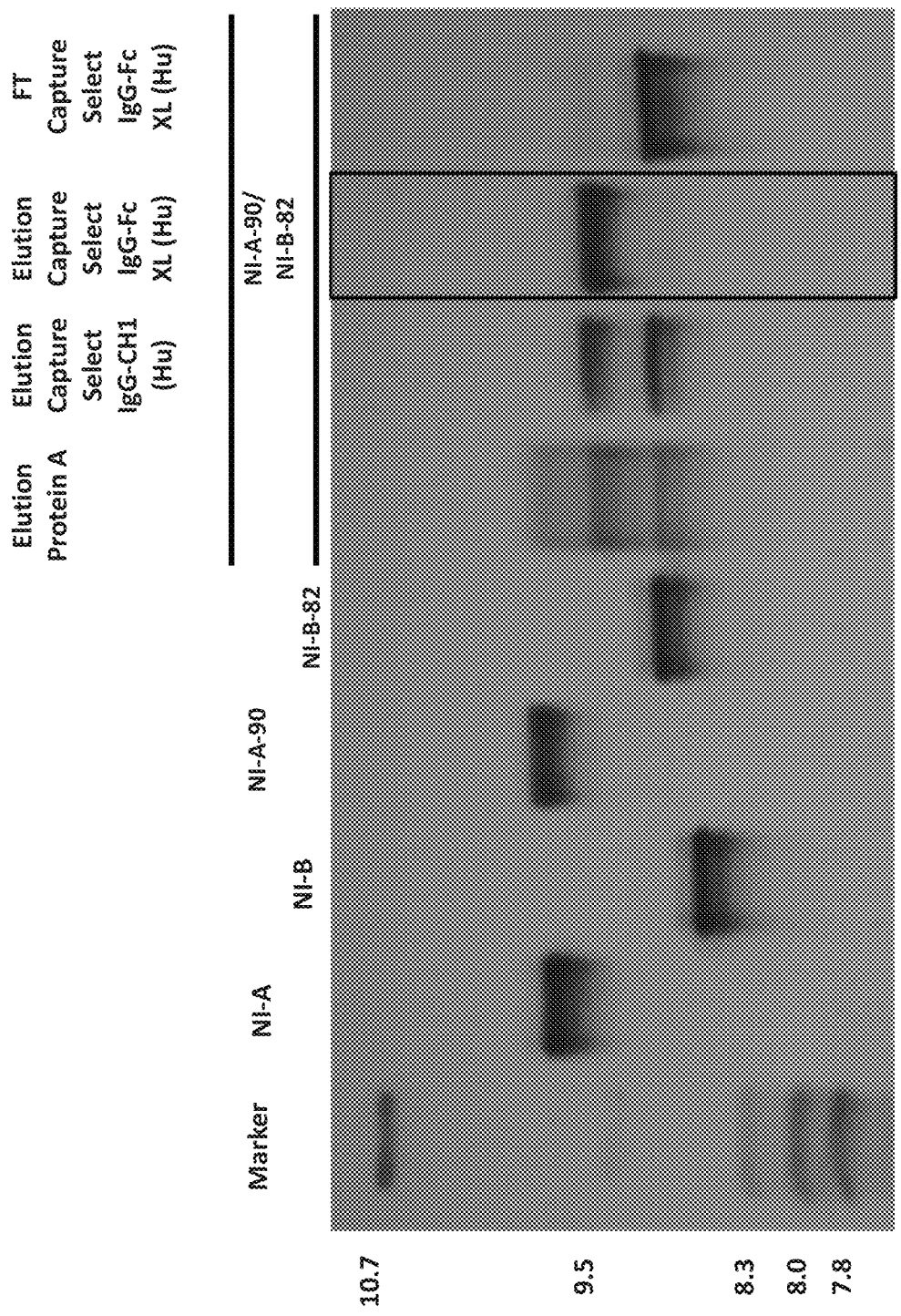
FIG. 17 is an isoelectric focusing polyacrylamide gel showing the asymmetric purification process of the bispecific antibody having the NI-A-90 and NI-B-82 parental monoclonal antibodies by two affinity steps with the CaptureSelect IgG-CH1 and CaptureSelect IgG Fc XL resins. Bispecific products are highlighted by boxes.
Figure 18:
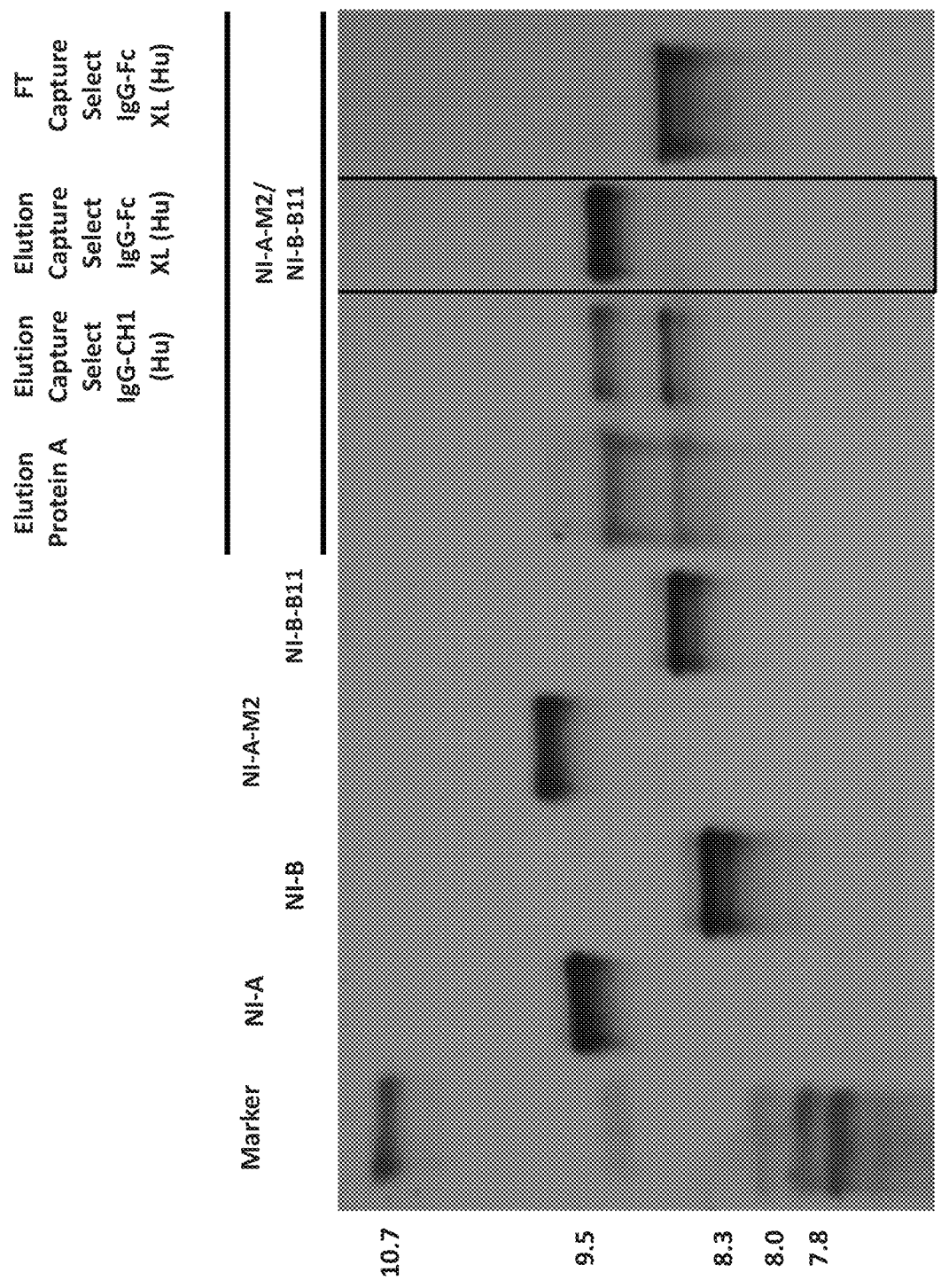
FIG. 18 is an isoelectric focusing polyacrylamide gel showing the asymmetric purification process of the bispecific antibody having the NI-A-M2 and NI-B-B11 parental monoclonal antibodies by two affinity steps with the CaptureSelect IgG-CH1 and CaptureSelect IgG Fc XL resins. Bispecific products are highlighted by boxes.

Therefore, all the fractions collected during the purification process were applied to a polyacrylamide IEF gel to separate the different antibody forms according to their isoelectric point, to have an overview of the efficiency of the purification process (FIGS. 17 and 18). As control, the WT IgG1 forms of NI-A and NI-B were used. Then, the two mutated parental monospecific forms were applied to verify their homogeneity. Difference between isoelectric points of control and mutated antibodies can be explained by the amino acid substitution introduced in IgG1 backbone and formulation buffers. The fractions collected from the protein A purification allow the visualization of the three different antibody species, the two monospecific antibodies migrating to their expected isoelectric points and an intermediate band corresponding to the bispecific forms as observed in FIGS. 17 and 18. Collected purified fractions obtained with the CaptureSelect IgG-CH1 contained the bispecific and CH3 monospecific forms as expected. Indeed, this step eliminated the parental mutated NI-A monoclonal antibodies having the CH1 mutation(s). NI-A-90 (FIG. 17) and NI-A-M2 (FIG. 18). Then, the collected purified fractions obtained with the CaptureSelect IgG-Fc XL allowed to isolate the bispecific antibodies with single (NI-A-90/NI-B-82, FIG. 17) and with double mutations (NI-A-M2/NI-B-B11, FIG. 18) to apparent homogeneity. This final step eliminated the parental mutated monoclonal antibody contaminants carrying the CH3 mutation(s), NI-B-82 (FIG. 17) and NI-A-B11 (FIG. 18), which were found in the flow-through. These results demonstrated that this novel two-step purification approach can efficiently isolate bispecific antibody having a common light chain and two different heavy chains to homogeneity without contaminations of monospecific forms.

Example 9

Determination of Bispecific IgG Thermal Stability

Figure 19:
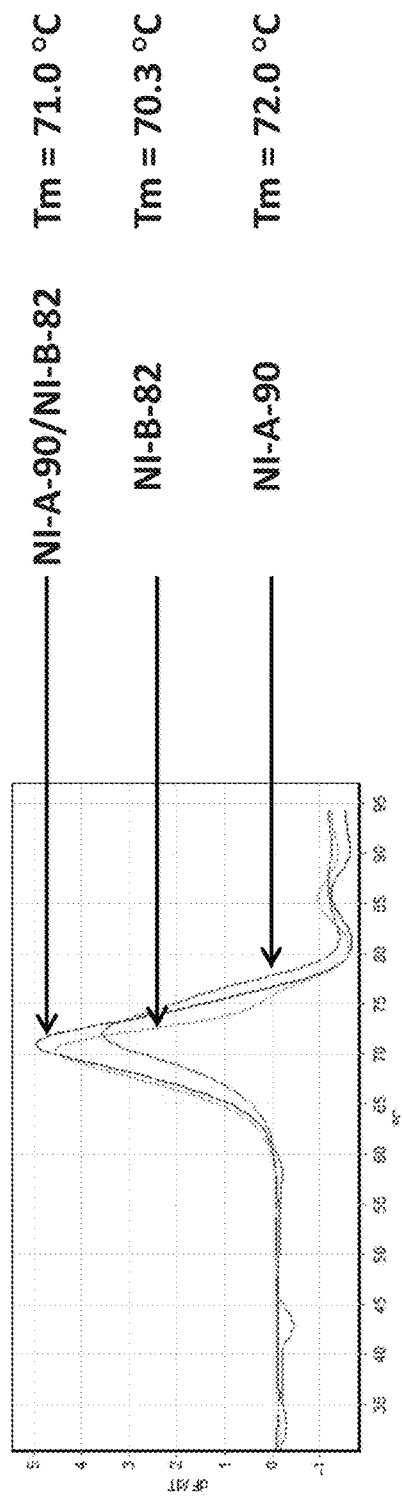
FIGS. 19A and 19B are a series of graphs showing the thermal stability of the bispecific NI-A-90/NI-B-80 antibody compared to the parental monoclonal antibody NI-A-90 and NI-B-82 (FIG. 19A) the thermal stability of the bispecific NI-A-M2/NI-B-B11 antibody compared to the parental monoclonal antibody NI-A-M2 and NI-B-B11 (FIG. 19B) determined by differential scanning fluorimetry.
Figure 19:
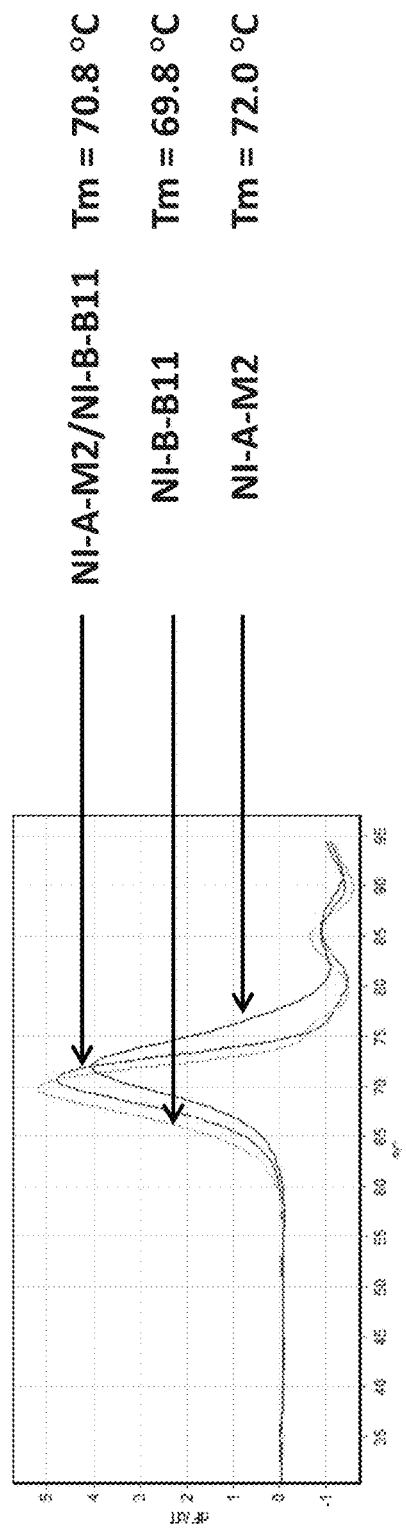

To control the quality of these bispecific antibodies, the thermal stability of the different variants was analyzed using DSF technology. Each bispecific antibody has been analyzed and compared to the two corresponding mutated monospecific parental antibodies. NI-A-90 and NI-B-82 were compared to the bispecific antibody carrying the single mutations (NI-A-90/NI-B-82) (FIG. 19A), and NI-A-M2 and NI-B-B11 to the bispecific antibody carrying the double mutations (NI-A-M2/NI-B-B11) (FIG. 19B). In both cases and as anticipated, the bispecific antibodies have an intermediate thermal stability compared to monospecific forms. These results further confirm that homogeneous bispecific antibodies have been obtained.

Example 10

Figure 20:
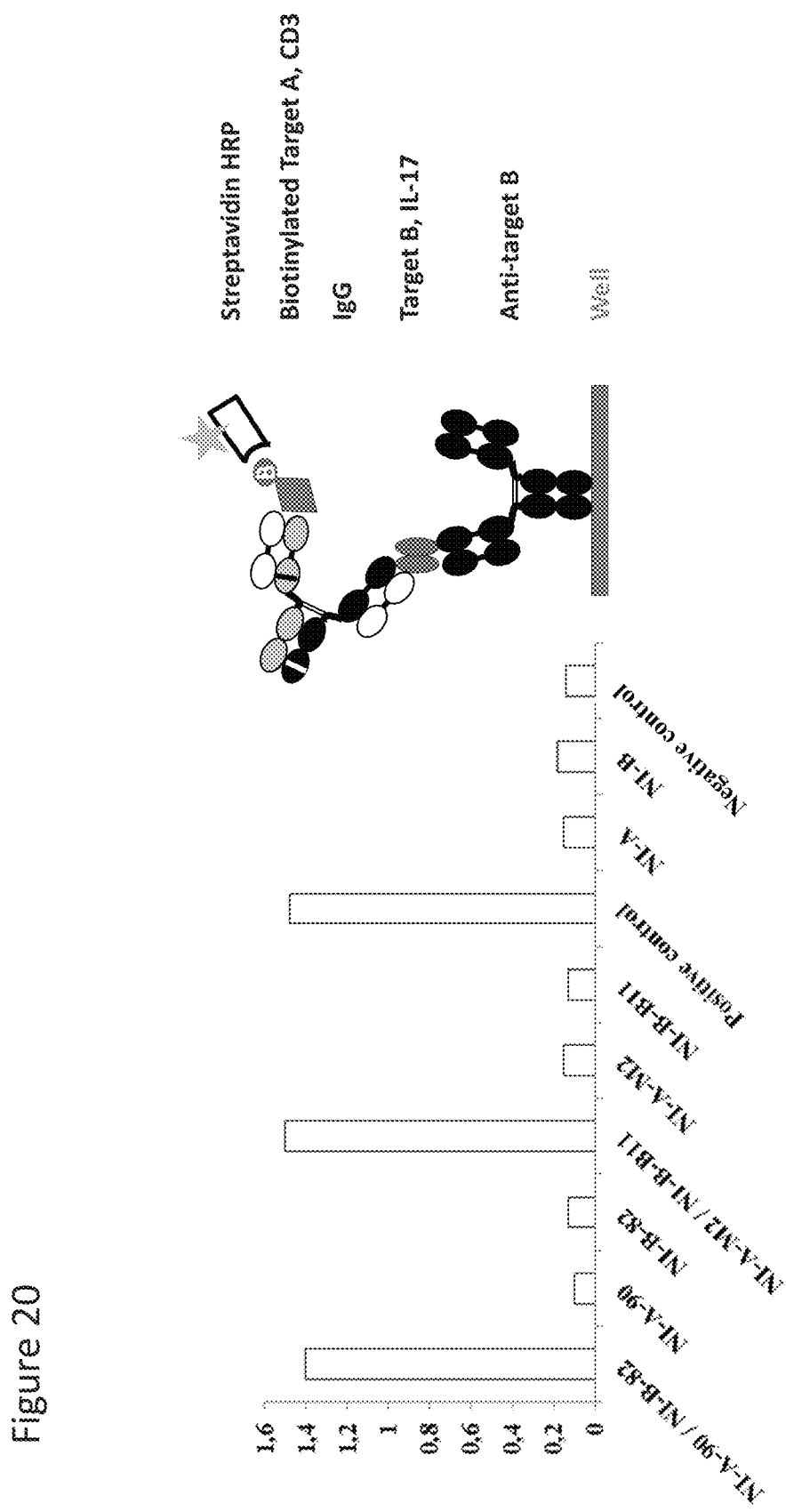
FIG. 20 is a graph depicting the co-engagement of target A and B by the NI-A-90/NI-B-80 and NI-A-M2/NI-B-B11 bispecific antibodies determined by ELISA.

Bispecific IgG Obtained by Asymmetric Purification can Co-Engage Two Different Targets The selected bispecific antibodies share a common light chain and have one heavy chain from the NI-A, carrying the CH1 mutation(s) and targeting the CD3, and the other one of the NI-B having the CH3 mutation(s) and binding to the IL-17. To verify the ability of the bsAbs to co-engage these two targets, an ELISA assay was performed (FIG. 20). Anti-IL-17 mAbs were coated on wells before sequential additions of IL-17, IgGs (parental WT monoclonal IgGs, parental mutated monoclonal IgGs, corresponding bispecific antibodies, positive bispecific antibody control obtained using the Knob-into-Hole technology described in U.S. Pat.

Figure 21:
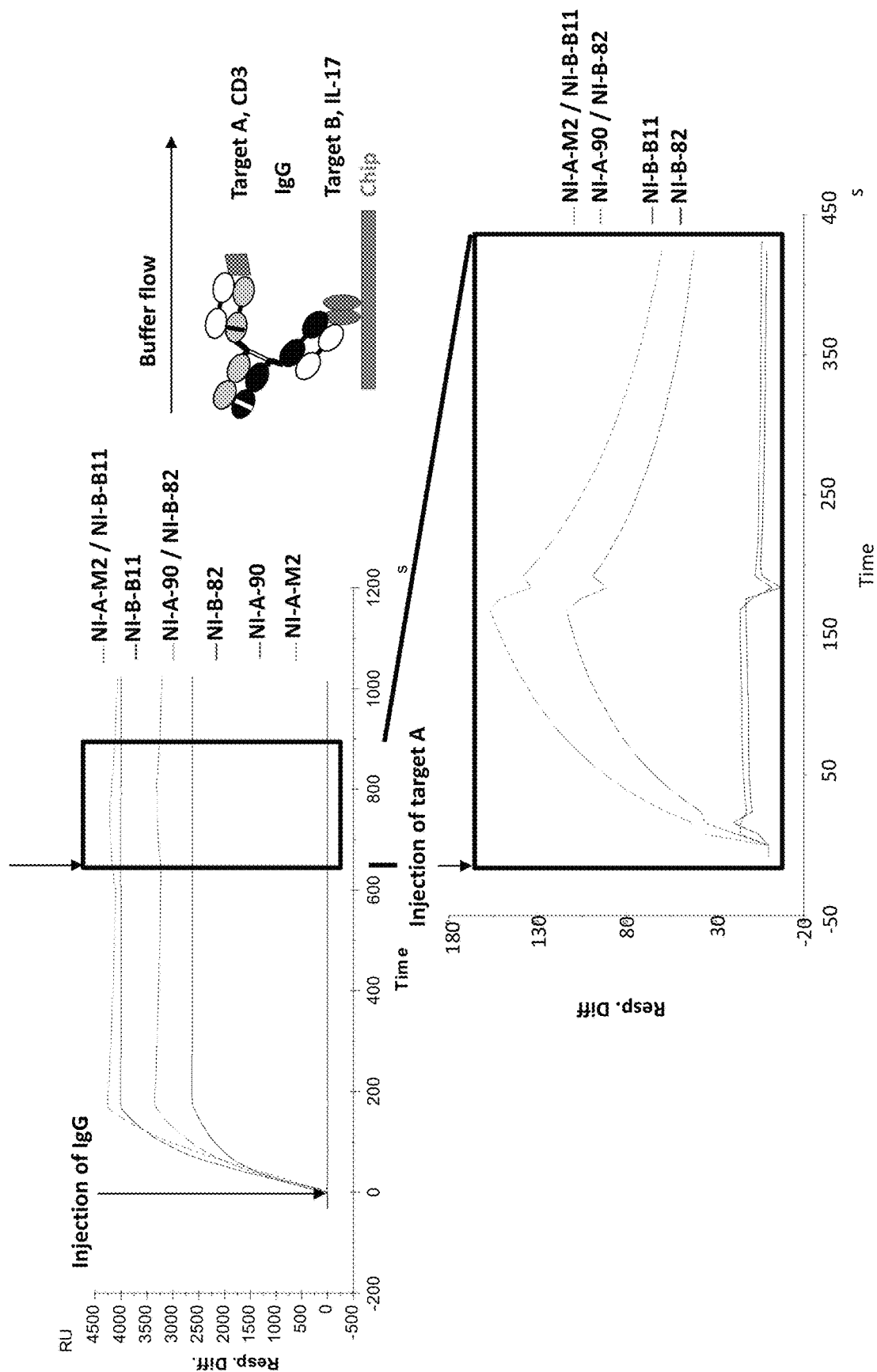
FIG. 21 is graphs depicting the co-engagement of target A and B by the NI-A-90/NI-B-80 and NI-A-M2/NI-B-B11 bispecific antibodies determined by Biacore.

No. 8,216,805 B2 patent and negative control IgG) biotinylated CD3 proteins and streptavidin coupled to horseradish peroxidase. After incubations, the reaction was revealed by addition of TMB substrate and the OD was measured at 450 nm. Results presented in FIG. 20 showed that monospecific antibodies gave a signal similar to the negative control. In contrast, similar signals were obtained for the purified bispecific antibodies and the positive control indicating that the bispecific antibodies NI-A-90/NI-B-82 and NI-A-M2/NI-B-B11 are able to co-engage CD3 and IL-17. To confirm these data, a co-engagement assay has been performed using Biacore (FIG. 21). IgGs were injected and captured on the IL-17 coated surface (FIG. 21), leading to an association curve for the monospecific (NI-B-82 and NI-B-B11) and the bispecific forms (NI-A-90/NI-B-82 and NI-A-M2/NI-B-B11), carrying the heavy chain from the NI-B. In contrast, no binding was observed for the monospecific forms used as negative control, NI-A-90 and NI-A-M2, which bind to CD3. Afterward, recombinant human CD3 proteins were injected resulting in a second association curve for the bispecific antibodies but not for the monospecific forms NI-B-82 and NI-B-B11 (FIG. 21). This assay confirmed that produced bispecific antibodies can co-engage their two targets.

Example 11

Figure 22:
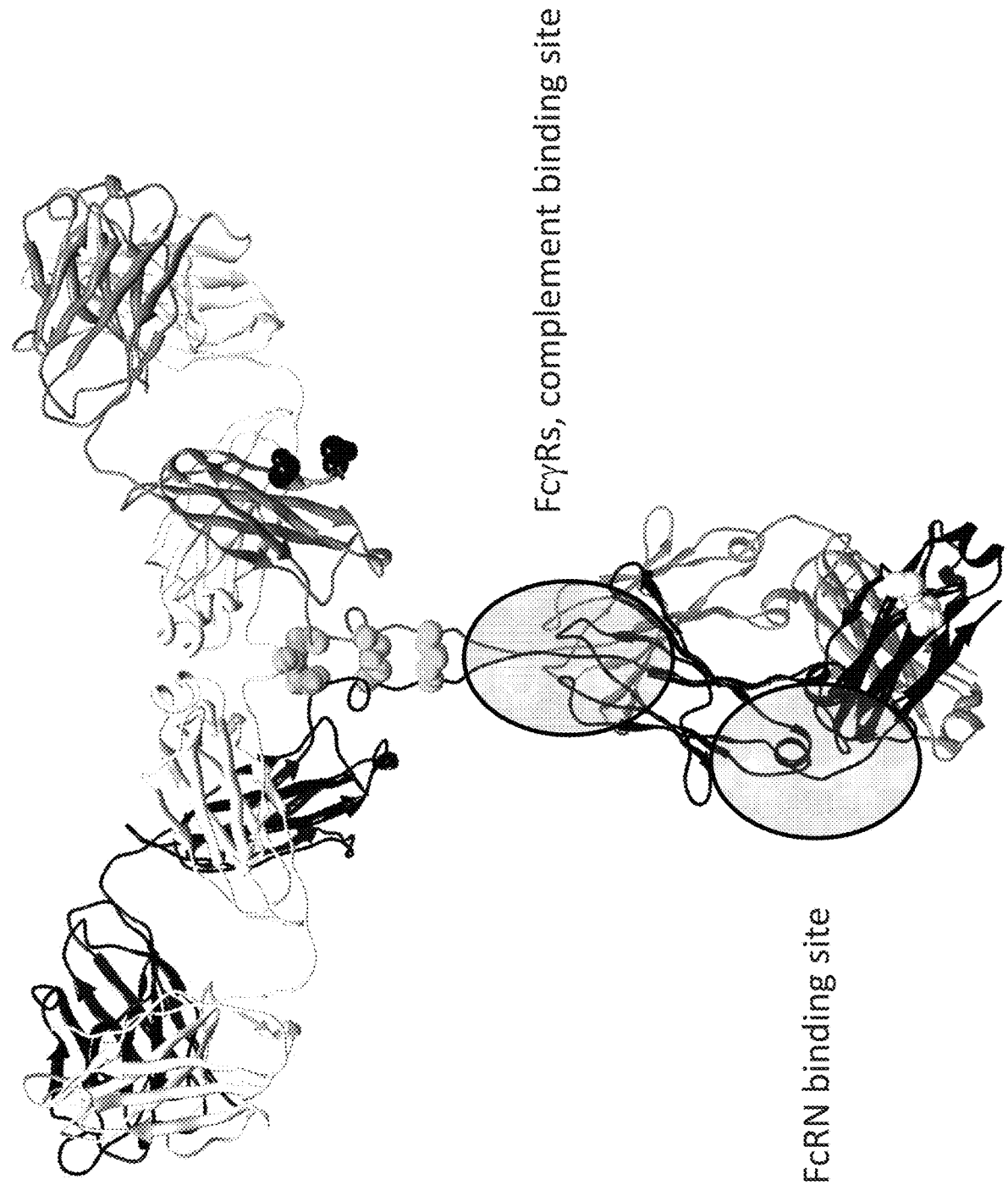
FIG. 22 is an illustration depicting an example of an IgG1 bispecific antibody having mutations in one CH1 domain of the first heavy chain at position 40 (40S) and position 47 (47T) and mutations in one CH3 domain of the second heavy chain at position 265 (265E) and position 270 (270P).

Mutations Introduced in the CH1 and CH3 Domains of Bispecific IgG do not Overlap with IgG FcRn Binding Site Bispecific antibodies having an IgG format can mediate Fc-mediated effector functions. In addition, interaction of the Fc region with FcRn increases IgG half-life in the circulation. The introduction of mutation(s) in the constant regions of an IgG can potentially alter binding to human FcγRs, complement and FcRn. These interactions occur at the junction between the hinge region and the CH2 domain for FcγRs and complement, and through an epitope comprising residues which are at the interface between the CH2 and CH3 domains for FcRn (FIG. 22). Mutations introduced in the IgG constant region were mapped on an IgG structure (FIG. 22). Mutations 90 and M2 in the CH1 domain and 82 and B11 in the CH3 domain are not localized in IgG epitopes important for binding to FcγRs, complement and FcRn (FIG. 22). These data suggest that bispecific antibodies containing the mutations 90, M2, 82 and B11 should have biological functions similar to WT IgG.

Example 12

Figure 23:
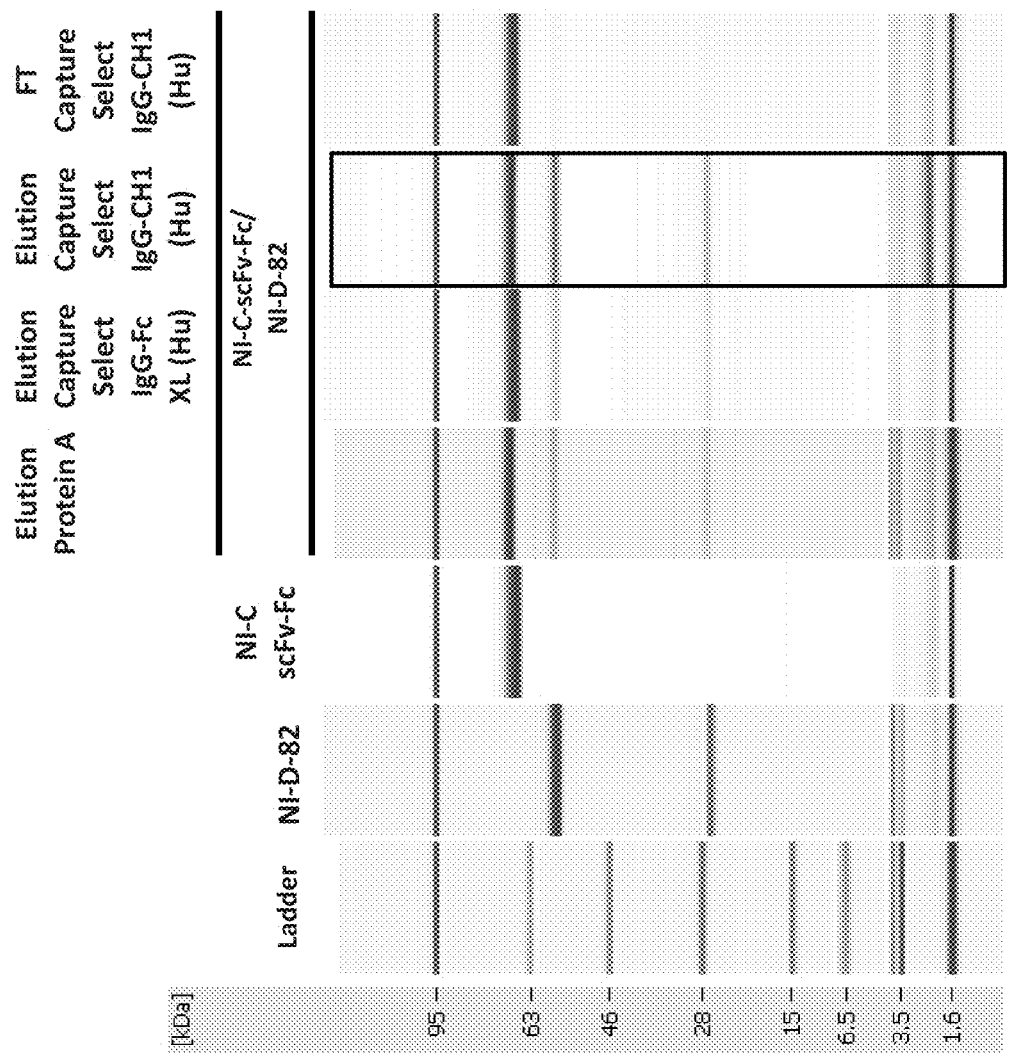
FIG. 23 is gel-like image representation of a protein 230 chip run monitoring the sizes of the parental monoclonal NI-D-82 and the NI-C-scFv-Fc polypeptide as well as bispecific antibody in denaturing and reducing conditions. Bispecific products are highlighted by boxes.

Production and Asymmetric Purification of Bispecific IgG Having One Light Chain, One Heavy Chain which Associates with the Light Chain and was Modified in its CH3 Domain and One Polypeptide Containing an Epitope Binding Region and an IgG Fc Region Composed of CH2 and CH3 Domains but Devoid of any CH1 Domain Like scFv-Fc To establish a second proof-of-concept, a bispecific antibody having one heavy chain, one associated light chain and one scFv-Fc polypeptide devoid of any CH1 domain was produced and purified. For this purpose, the VH and VL sequences of an NI-C antibody were associated in a scFv format which was further fused to an IgG1 Fc region composed of one CH2 and one CH3 domains. The sequence encoding the NI-C scFv-Fc polypeptide was then cloned into an expression vector. Afterward, the 82 mutation in the CH3 domain corresponding to IgG1 E265A was introduced into an expression vector encoding the NI-D antibody having one Kappa light chain and one IgG1 heavy chain. Then, a transient co-transfection was performed in mammalian cell with two vectors encoded the NI-C-scFv-Fc and the NI-D-82 antibody in order to generate a mixture of 3 polypeptide dimers, one parental monospecific IgG form, one parental monospecific scFv-Fc dimer and one bispecific form. Bispecific antibody was then purified and isolated from the supernatant by performing the two-steps asymmetric purification process using the Capture Select IgG-CH1 and then CaptureSelect IgG-Fc XL affinity matrix. In parallel to the two-step process, a protein A purification was performed on aliquot of supernatant containing the antibody mixture to isolate the three different species. A gel analysis in reducing and denaturing conditions was performed (FIG. 23). As expected, two bands are detected for the parental monoclonal NI-D-82 antibody one at 23 kDa and one at 55 kDa corresponding to the light and the heavy chains, respectively. For the NI-C-scFv-Fc, only one band is detected as predicted (65 kDa). The fractions collected from the protein A purification allow the visualization of the three different bands corresponding to light and heavy chains of the NI-D-82 and the NI-C-scFv-Fc. As expected, three bands are also observed for bispecific antibodies after the two-steps asymmetric purification process using the Capture Select IgG-CH1 and then CaptureSelect IgG-Fc XL affinity matrix, the first at 23 kDa for LCs, the second at 55 kDa for the HC of the NI-D and the third at 65 kDa for the scFv-Fc of the NI-C.

Figure 24:
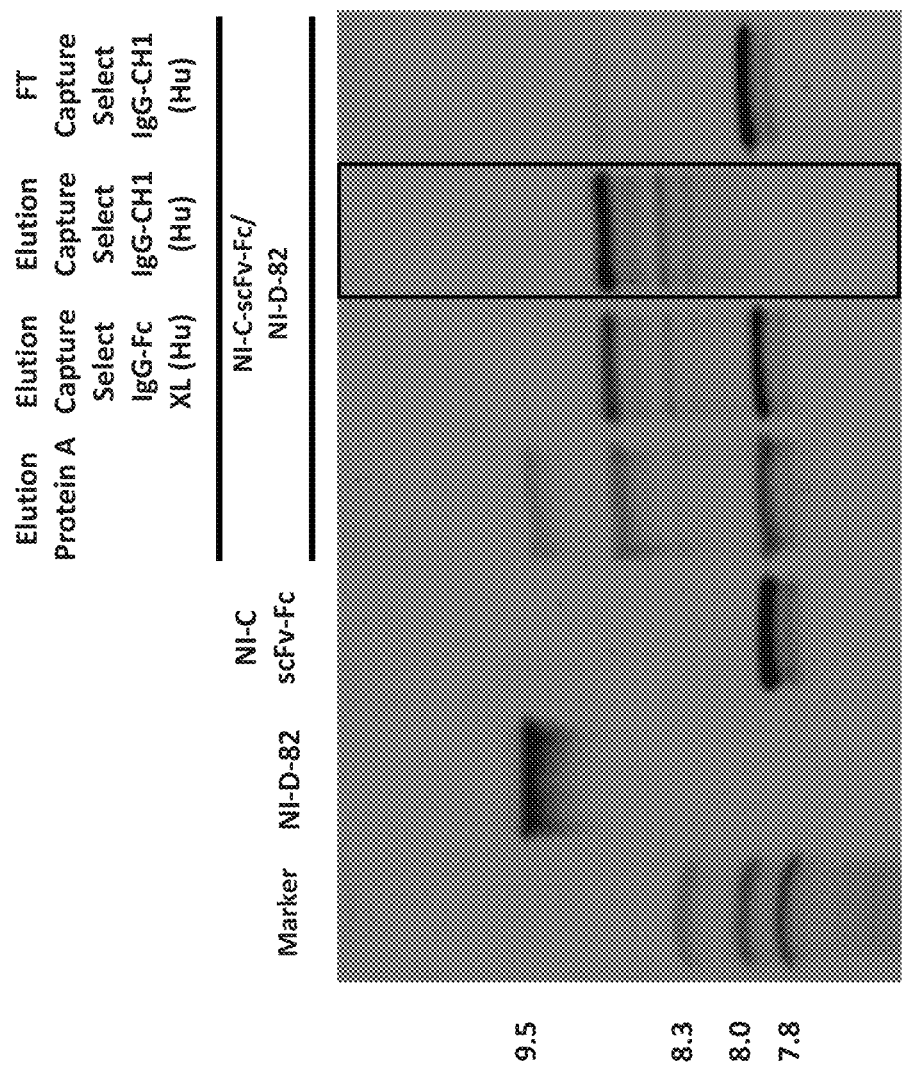
FIG. 24 is an isoelectric focusing polyacrylamide gel showing the asymmetric purification process of the bispecific antibody having the NI-C-scFv-Fc polypeptide and NI-D-82 parental monoclonal antibody by two affinity steps with the CaptureSelect IgG Fc XL and CaptureSelect IgG-CH1 resins. Bispecific product is highlighted by a box.

To have an overview of the efficiency of the purification strategy, all the fractions collected during the purification process were applied to a polyacrylamide IEF gel to separate the different antibody forms according to their isoelectric point (FIG. 24). As control, the mutated IgG1 form of NI-D and the scFv-Fc dimer of NI-C were used. The fractions collected from the protein A purification allow the visualization of the three different antibody species, the two monospecific antibodies migrating to their expected isoelectric points and an intermediate band corresponding to the bispecific forms as observed in FIG. 24. Collected purified fractions obtained with the CaptureSelect IgG-Fc XL contained the bispecific and NI-C-scFv-Fc monospecific forms as expected. Indeed, this step eliminated the monoclonal antibody contaminant which is the parental NI-D-82 carrying the CH3 mutation in its two CH3 domains. Then, the collected purified fractions obtained with the CaptureSelect IgG-CH1 allowed to isolate the bispecific antibody having one heavy chain, one light chain and one scFv-Fc to apparent homogeneity. This final step eliminated the scFv-Fc dimer of NI-C as this polypeptide does not have any CH1 domain and was found in the flow-through as expected. These results demonstrated that this novel two-step purification approach can efficiently isolate bispecific antibody to homogeneity without contaminations of monospecific forms. This bispecific format is composed of one heavy chain, one associated light chain and one polypeptide containing an epitope binding region and an IgG-Fc region having CH2 and CH3 domains but devoid of any CH1 domain like scFv-Fc.

What is claimed is:

1. A method for producing a bispecific antigen-binding protein, the method comprising:
   a) obtaining a first nucleic acid sequence encoding a polypeptide comprising a first variable domain that recognizes a first epitope and an IgG1, IgG2, IgG3 or IgG4 isotype constant domain that does not include an immunoglobulin constant CH1 domain of a human IgG selected from IgG1 IgG2, IgG3 and IgG4, which therefore eradicates binding to the ligand of a specific CH1 chromatography media or any affinity reagent interacting with the human IgG1, IgG2, IgG3 and IgG4 CH1 domain;
   b) obtaining a second nucleic acid sequence encoding a second polypeptide comprising a second epitope-binding region that selectively binds a second epitope and an IgG1, IgG2, IgG3 or IgG4 isotype constant domain that comprises a modification in its CH3 domain that eradicates or reduces binding to the ligand of a specific CH3 chromatography media or any affinity reagent interacting with the human IgG1, IgG2, IgG3 and IgG4 CH3 domain;
   c) obtaining a third nucleic acid sequence encoding an immunoglobulin light chain that pairs with the second immunoglobulin heavy chain;
   d) introducing the first, second, and third nucleic acid sequences into a mammalian cell;
   e) allowing the cell to express a bispecific antigen-binding protein;
   f) isolating the bispecific antigen-binding protein based on the ability of the bispecific antibody to bind to the ligand of a specific CH1 chromatography media or any affinity reagent interacting with the human IgG1, IgG2, IgG3 and IgG4 CH1 domain; and
   g) isolating the bispecific antigen-binding protein based on the ability of the bispecific antibody to bind to the ligand of a specific CH3 chromatography media or any affinity reagent interacting with the human IgG1, IgG2, IgG3 and IgG4 CH3 domain,
   wherein the CH3 domain of the second polypeptide is selected from the group consisting of (i) an IgG1 CH3 domain, wherein the modification in the IgG1 CH3 domain of the second polypeptide comprises an E42A mutation in the IMGT exon numbering system or a E42Q mutation in the IMGT exon numbering system, a P47T in the IMGT exon numbering system or a combination thereof; (ii) an IgG2 CH3 domain, wherein the modification in the CH3 domain of the second IgG2 heavy chain comprises an E42A mutation in the IMGT exon numbering system or a E42Q mutation in the IMGT exon numbering system, a P47T in the IMGT exon numbering system or a combination thereof; (iii) an IgG3 CH3 domain, wherein the modification in the CH3 domain of the second IgG3 heavy chain comprises an E42A mutation in the IMGT exon numbering system or a E42Q mutation in the IMGT exon numbering system, a P47T in the IMGT exon numbering system or a combination thereof; and (iv) an IgG4 CH3 domain, and wherein the modification in the CH3 domain of the second IgG4 heavy chain comprises an E42A mutation in the IMGT exon numbering system or a E42Q mutation in the IMGT exon numbering system, a P47T in the IMGT exon numbering system or a combination thereof.

2. The method of claim 1, wherein the affinity reagent interacting with the human IgG1, IgG2, IgG3 and IgG4 CH1 domain comprises an affinity resin.

3. The method of claim 2, wherein the affinity resin is an aldehyde-activated agarose resin having a particle size of 70 μm, wherein the aldehyde-activated agarose resin specifically binds to human IgG-CH1 region.

4. The method of claim 2, wherein the bispecific antigen-binding protein is isolated on a solid support comprising an IgG-CH1 specific affinity reagent or any affinity reagent interacting with the human IgG1, IgG2, IgG3 and IgG4 CH1 domain, wherein the IgG-CH1 specific affinity reagent comprises an aldehyde-activated agarose resin having a particle size of 70 μm, wherein the aldehyde-activated agarose resin specifically binds to human IgG-CH1 region.

5. The method of claim 4, wherein the solid support comprises IgG-CH1 affinity column, or any affinity reagent interacting with the human IgG1, IgG2, IgG3 and IgG4 CH1 domain, and the bispecific antigen-binding protein is isolated employing a pH gradient, wherein the IgG1-CH1 specific affinity column comprises an aldehyde-activated agarose resin having a particle size of 70 μm, wherein the aldehyde-activated agarose resin specifically binds to human IgG-CH1 region.

6. The method of claim 1, wherein the affinity reagent interacting with the human IgG1, IgG2, IgG3 and IgG4 CH3 domain comprises an affinity resin.

7. The method of claim 6, wherein the affinity resin is an aldehyde-activated agarose resin having a particle size of 65 μm, wherein the aldehyde-activated agarose resin specifically binds to human IgG-CH3 region.

8. The method of claim 6, wherein the bispecific antigen-binding protein is isolated on a solid support comprising an IgG-CH3 specific affinity reagent, or any affinity reagent interacting with the human IgG1, IgG2, IgG3 and IgG4 CH3 domain, wherein the IgG-CH3 specific affinity reagent comprises an aldehyde-activated agarose resin having a particle size of 65 μm, wherein the aldehyde-activated agarose resin specifically binds to human IgG-CH3 region.

9. The method of claim 8, wherein the solid support comprises an IgG-CH3 specific affinity column, or any affinity reagent interacting with the human IgG1, IgG2, IgG3 and IgG4 CH3 domain, and the bispecific antigen-binding protein is isolated employing a pH gradient, wherein the IgG1-CH3 specific affinity column comprises an aldehyde-activated agarose resin having a particle size of 65 μm, wherein the aldehyde-activated agarose resin specifically binds to human IgG-CH3 region.

10. A method for producing a bispecific antibody comprising:
    a) obtaining a first nucleic acid sequence encoding a first immunoglobulin heavy chain comprising a first variable domain that recognizes a first epitope, wherein the first immunoglobulin heavy chain comprises an IgG1, IgG2, IgG3 or IgG4 isotype constant domain that comprises a modification in its CH1 domain that eradicates or reduces binding to the ligand of a specific CH1 chromatography media comprising an IgG-CH1 specific affinity reagent, or any affinity reagent interacting with the human IgG1, IgG2, IgG3 and IgG4 CH1 domain, wherein the IgG-CH1 specific affinity reagent comprises an aldehyde-activated agarose resin having a particle size of 70 μm, wherein the aldehyde-activated agarose resin specifically binds to human IgG-CH1 region;
    b) obtaining a second nucleic acid sequence encoding a second immunoglobulin heavy chain comprising a second variable domain that recognizes a second epitope, wherein the second immunoglobulin heavy chain comprises an IgG1, IgG2, IgG3 or IgG4 isotype constant domain that comprises a modification in its CH3 domain that eradicates or reduces binding to the ligand of a specific CH3 chromatography media comprising an IgG-CH3 specific affinity reagent, or any affinity reagent interacting with the human IgG1, IgG2, IgG3 and IgG4 CH3 domain, wherein the IgG-CH3 specific affinity reagent comprises an aldehyde-activated agarose resin having a particle size of 65 μm, wherein the aldehyde-activated agarose resin specifically binds to human IgG-CH3 region;
    c) obtaining a third nucleic acid sequence encoding an immunoglobulin a light chain that pairs with the first and the second immunoglobulin heavy chain;
    d) introducing the first, second, and third nucleic acid sequences into a mammalian cell;
    e) allowing the cell to express a bispecific antibody;
    f) isolating the bispecific antibody based on the ability of the bispecific antibody to bind to the ligand of a first specific CH1 chromatography media an IgG-CH1 specific affinity reagent, or any affinity reagent interacting with the human IgG1, IgG2, IgG3 and IgG4 CH1 domain, wherein the IgG-CH1 specific affinity reagent comprises an aldehyde-activated agarose resin having a particle size of 70 μm, wherein the aldehyde-activated agarose resin specifically binds to human IgG-CH1 region; and
    g) isolating the bispecific antibody based on the ability of the bispecific antibody to bind to the ligand of a second specific CH3 chromatography media comprising an IgG-CH3 specific affinity reagent, or any affinity reagent interacting with the human IgG1, IgG2, IgG3 and IgG4 CH3 domain, wherein the IgG-CH3 specific affinity reagent comprises an aldehyde-activated agarose resin having a particle size of 65 μm, wherein the aldehyde-activated agarose resin specifically binds to human IgG-CH3 region,
    wherein the modification in the CH1 domain of the first heavy chain comprises an S40E mutation in the IMGT exon numbering system.

11. The method of claim 10, wherein the first CH1 domain of the bispecific antibody, the second CH1 domain or both the first and second CH1 domains are non-immunogenic in a human.

12. The method of claim 10, wherein the affinity reagent interacting with the human IgG1, IgG2, IgG3 and IgG4 CH1 domain comprises an affinity resin.

13. The method of claim 12, wherein the affinity resin is an aldehyde-activated agarose resin having a particle size of 70 μm, wherein the aldehyde-activated agarose resin specifically binds to human IgG-CH1 region.

14. The method of claim 12, wherein the bispecific antibody is isolated on a solid support comprising an IgG-CH1 specific affinity reagent or any affinity reagent interacting with the human IgG1, IgG2, IgG3 and IgG4 CH1 domain, wherein the IgG-CH1 specific affinity reagent comprises an aldehyde-activated agarose resin having a particle size of 70 μm, wherein the aldehyde-activated agarose resin specifically binds to human IgG-CH1 region.

15. The method of claim 14, wherein the solid support comprises IgG-CH1 affinity column, or any affinity reagent interacting with the human IgG1, IgG2, IgG3 and IgG4 CH1 domain, and the bispecific antigen-binding protein is isolated employing a pH gradient, wherein the IgG1-CH1 specific affinity column comprises an aldehyde-activated agarose resin having a particle size of 70 μm, wherein the aldehyde-activated agarose resin specifically binds to human IgG-CH1 region.

16. The method of claim 10, wherein the CH3 domain of the second polypeptide is selected from the group consisting of (i) an IgG1 CH3 domain, wherein the modification in the CH3 domain of the second IgG1 heavy chain comprises an E42A mutation in the IMGT exon numbering system or a E42Q mutation in the IMGT exon numbering system, a P47T in the IMGT exon numbering system or a combination thereof; (ii) an IgG2 CH3 domain, wherein the modification in the CH3 domain of the second IgG2 heavy chain comprises an E42A mutation in the IMGT exon numbering system or a E42Q mutation in the IMGT exon numbering system, a P47T in the IMGT exon numbering system or a combination thereof; (iii) an IgG3 CH3 domain, and wherein the modification in the CH3 domain of the second IgG3 heavy chain comprises an E42A mutation in the IMGT exon numbering system or a E42Q mutation in the IMGT exon numbering system, a P47T in the IMGT exon numbering system or a combination thereof; and (iv) an IgG4 CH3 domain, and wherein the modification in the CH3 domain of the second IgG4 heavy chain comprises an E42A mutation in the IMGT exon numbering system or a E42Q mutation in the IMGT exon numbering system, a P47T in the IMGT exon numbering system or a combination thereof.

17. The method of claim 10, wherein the affinity reagent binding to the human IgG1, IgG2, IgG3 and IgG4 CH3 domain comprises an affinity resin.

18. The method of claim 17, wherein the affinity resin is an aldehyde-activated agarose resin having a particle size of 65 μm, wherein the aldehyde-activated agarose resin specifically binds to human IgG-CH3 region.

19. The method of claim 17, wherein the bispecific antigen-binding protein is isolated on a solid support comprising an IgG-CH3 specific affinity reagent, or any affinity reagent interacting with the human IgG1, IgG2, IgG3 and IgG4 CH3 domain, wherein the IgG-CH3 specific affinity reagent comprises an aldehyde-activated agarose resin having a particle size of 65 μm, wherein the aldehyde-activated agarose resin specifically binds to human IgG-CH3 region.

20. The method of claim 19, wherein the solid support comprises an IgG-CH3 specific affinity column, or any affinity reagent interacting with the human IgG1, IgG2, IgG3 and IgG4 CH3 domain, and the bispecific antigen-binding protein is isolated employing a pH gradient, wherein the IgG1-CH3 specific affinity column comprises an aldehyde-activated agarose resin having a particle size of 65 μm, wherein the aldehyde-activated agarose resin specifically binds to human IgG-CH3 region.

21. A method for isolating a bispecific antibody, comprising isolating from a disrupted cell or a mixture of antibodies, having:
   a) a bispecific antibody comprising: i) a first heavy chain comprising a modified IgG1, IgG2, IgG3 or IgG 4 CH3 domain, and ii) a second heavy chain comprising a modified IgG1, IgG2, IgG3 or IgG4 CH1 domain or no CH1 domain;
   b) a monospecific antibody comprising two copies of a heavy chains comprising a modified IgG1, IgG2, IgG3 or IgG4 CH3 domain; and
   c) a monospecific antibody comprising two copies of a heavy chain comprising a modified IgG1, IgG2, IgG3 or IgG4 CH1 domain or no CH1 domain, wherein the modified CH1 and CH3 domains are non-immunogenic in a human, and wherein the heavy chain comprising a modified CH1 or no CH1 domain, and the heavy chain comprising a modified CH3 domain results in a bispecific antibody with a heterodimeric heavy chain constant region whose monomers have a differential affinity for an affinity reagent binding to the human IgG1, IgG2, IgG3 and IgG4 CH1 domain, and have a differential affinity for an affinity reagent binding to the human IgG1, IgG2, IgG3 and IgG4 CH3 domain,
   wherein the modification in the CH1 domain of the first heavy chain comprises an S40E mutation in the IMGT exon numbering system, and the modified CH3 domain is selected from the group consisting of:
   a) an IgG1 CH3 domain, comprising an E42A mutation, a P47T mutation or a combination thereof, using the numbering according to SEQ ID NO: 9;
   b) an IgG2 CH3 domain, comprising an E42A mutation, an E42Q mutation, a P47T mutation or a combination thereof, using the numbering according to SEQ ID NO: 10:
   c) an IgG3 CH3 domain, comprising an E42A mutation, an E42Q mutation, a P47T mutation or a combination thereof, using the numbering according to SEQ ID NO: 11; and
   d) an IgG4 CH3 domain, comprising an E42A mutation, an E42Q mutation, a P47T mutation or a combination thereof using the numbering according to SEQ ID NO: 12.

22. The method of claim 1, wherein the CH3 domain of the second polypeptide is selected from the group consisting:
   a) an IgG1 CH3 domain, comprising an E42A mutation, a P47T mutation or a combination thereof, using the numbering according to SEQ ID NO: 9;
   b) an IgG2 CH3 domain, comprising an E42A mutation, an E42Q mutation, a P47T mutation or a combination thereof, using the numbering according to SEQ ID NO: 10;
   c) an IgG3 CH3 domain, comprising an E42A mutation, an E42Q mutation, a P47T mutation or a combination thereof, using the numbering according to SEQ ID NO: 11; and
   d) an IgG4 CH3 domain, comprising an E42A mutation, or an E42Q mutation, a P47T mutation or a combination thereof using the numbering according to SEQ ID NO: 12.

23. The method of claim 10, wherein the second nucleic acid sequence encoding the second polypeptide that comprises a CH3 domain selected from the group consisting of:
   a) an IgG1 CH3 domain, comprising an E42A mutation, a P47T mutation or a combination thereof, using the numbering according to SEQ ID NO: 9;
   b) an IgG2 CH3 domain, comprising an E42A mutation, an E42Q mutation or a P47T mutation or a combination thereof, using the numbering according to SEQ ID NO: 10;
   c) an IgG3 CH3 domain, comprising an E42A mutation, an E42Q mutation, a P47T mutation or a combination thereof, using the numbering according to SEQ ID NO: 11; and
   d) an IgG4 CH3 domain, comprising an E42A mutation, an E42Q mutation, a P47T mutation or a combination thereof using the numbering according to SEQ ID NO: 12.

* * * * *

SEQUENCE LISTING

<160> NUMBER OF SEQ ID NOS: 20

<210> SEQ ID NO 1
<211> LENGTH: 98
<212> TYPE: PRT
<213> ORGANISM: Homo sapiens

<400> SEQUENCE: 1

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val
```

<210> SEQ ID NO 2
<211> LENGTH: 98
<212> TYPE: PRT
<213> ORGANISM: Homo sapiens

<400> SEQUENCE: 2

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val
```

<210> SEQ ID NO 3
<211> LENGTH: 98
<212> TYPE: PRT
<213> ORGANISM: Homo sapiens

<400> SEQUENCE: 3

```
Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
```

```
                65                  70                  75                  80
Tyr Thr Cys Asn Val Asn His Lys Pro Ser Asn Thr Lys Val Asp Lys
                    85                  90                  95

Arg Val

<210> SEQ ID NO 4
<211> LENGTH: 98
<212> TYPE: PRT
<213> ORGANISM: Homo sapiens

<400> SEQUENCE: 4

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val

<210> SEQ ID NO 5
<211> LENGTH: 98
<212> TYPE: PRT
<213> ORGANISM: Homo sapiens

<400> SEQUENCE: 5

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Glu Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 6
<211> LENGTH: 98
<212> TYPE: PRT
<213> ORGANISM: Homo sapiens

<400> SEQUENCE: 6

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Glu Trp Asn Ser Gly Ala Leu Thr Ser
            35                  40                  45
```

```
Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val

<210> SEQ ID NO 7
<211> LENGTH: 98
<212> TYPE: PRT
<213> ORGANISM: Homo sapiens

<400> SEQUENCE: 7

Ala Ser Thr Lys Gly Pro Ser Val Phe Pro Leu Ala Pro Cys Ser Arg
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Glu Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
 65                  70                  75                  80

Tyr Thr Cys Asn Val Asn His Lys Pro Ser Asn Thr Lys Val Asp Lys
                 85                  90                  95

Arg Val

<210> SEQ ID NO 8
<211> LENGTH: 98
<212> TYPE: PRT
<213> ORGANISM: Homo sapiens

<400> SEQUENCE: 8

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                20                  25                  30

Phe Pro Glu Pro Val Thr Val Glu Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val

<210> SEQ ID NO 9
<211> LENGTH: 105
<212> TYPE: PRT
<213> ORGANISM: Homo sapiens

<400> SEQUENCE: 9

Gly Gln Pro Arg Glu Pro Gln Val Tyr Thr Leu Pro Pro Ser Arg Asp
 1               5                  10                  15
```

```
Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
 50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro
            100                 105
```

<210> SEQ ID NO 10
<211> LENGTH: 105
<212> TYPE: PRT
<213> ORGANISM: Homo sapiens

<400> SEQUENCE: 10

```
Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Met Leu Asp Ser Asp Gly Ser Phe
 50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro
            100                 105
```

<210> SEQ ID NO 11
<211> LENGTH: 105
<212> TYPE: PRT
<213> ORGANISM: Homo sapiens

<400> SEQUENCE: 11

```
Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Ser Gly Gln Pro Glu
        35                  40                  45

Asn Asn Tyr Asn Thr Thr Pro Pro Met Leu Asp Ser Asp Gly Ser Phe
 50                  55                  60

Phe Leu Tyr Ser Lys Leu Thr Val Asp Lys Ser Arg Trp Gln Gln Gly
65                  70                  75                  80

Asn Ile Phe Ser Cys Ser Val Met His Glu Ala Leu His Asn Arg Phe
                85                  90                  95

Thr Gln Lys Ser Leu Ser Leu Ser Pro
            100                 105
```

<210> SEQ ID NO 12
<211> LENGTH: 105

```
<212> TYPE: PRT
<213> ORGANISM: Homo sapiens

<400> SEQUENCE: 12

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu
            100                 105

<210> SEQ ID NO 13
<211> LENGTH: 105
<212> TYPE: PRT
<213> ORGANISM: Homo sapiens

<400> SEQUENCE: 13

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Gln Ser Asn Gly Gln Thr Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro
            100                 105

<210> SEQ ID NO 14
<211> LENGTH: 105
<212> TYPE: PRT
<213> ORGANISM: Homo sapiens

<400> SEQUENCE: 14

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Ala Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
```

85                  90                  95

Thr Gln Lys Ser Leu Ser Leu Ser Pro
                100                 105

<210> SEQ ID NO 15
<211> LENGTH: 105
<212> TYPE: PRT
<213> ORGANISM: Homo sapiens

<400> SEQUENCE: 15

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
                20                  25                  30

Tyr Pro Ser Asp Ile Ala Val Glu Trp Gln Ser Asn Gly Gln Thr Glu
            35                  40                  45

Asn Asn Tyr Lys Thr Thr Pro Pro Met Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro
                100                 105

<210> SEQ ID NO 16
<211> LENGTH: 105
<212> TYPE: PRT
<213> ORGANISM: Homo sapiens

<400> SEQUENCE: 16

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
                20                  25                  30

Tyr Pro Ser Asp Ile Ala Val Glu Trp Ala Ser Asn Gly Gln Pro Glu
            35                  40                  45

Asn Asn Tyr Lys Thr Thr Pro Pro Met Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro
                100                 105

<210> SEQ ID NO 17
<211> LENGTH: 105
<212> TYPE: PRT
<213> ORGANISM: Homo sapiens

<400> SEQUENCE: 17

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
                20                  25                  30

Tyr Pro Ser Asp Ile Ala Val Glu Trp Gln Ser Ser Gly Gln Thr Glu
            35                  40                  45

Asn Asn Tyr Asn Thr Thr Pro Pro Met Leu Asp Ser Asp Gly Ser Phe
            50                  55                  60

Phe Leu Tyr Ser Lys Leu Thr Val Asp Lys Ser Arg Trp Gln Gln Gly
65                  70                  75                  80

Asn Ile Phe Ser Cys Ser Val Met His Glu Ala Leu His Asn Arg Phe
                85                  90                  95

Thr Gln Lys Ser Leu Ser Leu Ser Pro
            100                 105

<210> SEQ ID NO 18
<211> LENGTH: 105
<212> TYPE: PRT
<213> ORGANISM: Homo sapiens

<400> SEQUENCE: 18

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Ala Ser Ser Gly Gln Pro Glu
        35                  40                  45

Asn Asn Tyr Asn Thr Thr Pro Pro Met Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Ile Phe Ser Cys Ser Val Met His Glu Ala Leu His Asn Arg Phe
                85                  90                  95

Thr Gln Lys Ser Leu Ser Leu Ser Pro
            100                 105

<210> SEQ ID NO 19
<211> LENGTH: 105
<212> TYPE: PRT
<213> ORGANISM: Homo sapiens

<400> SEQUENCE: 19

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Gln Ser Asn Gly Gln Thr Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu
            100                 105

<210> SEQ ID NO 20
<211> LENGTH: 105
<212> TYPE: PRT
<213> ORGANISM: Homo sapiens

<400> SEQUENCE: 20

```
Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Ala Ser Asn Gly Gln Pro Glu
            35                  40                  45

Asn Asn Tyr Lys Thr Thr Pro Pro Val Leu Asp Ser Asp Gly Ser Phe
    50              55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu
            100             105
```